United States Patent
Nishioka et al.

(10) Patent No.: US 12,167,924 B2
(45) Date of Patent: Dec. 17, 2024

(54) MEDICAL IMAGE PROCESSING APPARATUS, RECORDING MEDIUM, AND SYSTEM

(71) Applicant: CANON MEDICAL SYSTEMS CORPORATION, Otawara (JP)

(72) Inventors: Takahiko Nishioka, Otawara (JP); Brian Mohr, Edinburgh (GB); Shintaro Niwa, Nasushiobara (JP); Joanne Schuijf, Zoetermeer (NL)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 370 days.

(21) Appl. No.: 17/132,403

(22) Filed: Dec. 23, 2020

(65) Prior Publication Data

US 2021/0196221 A1 Jul. 1, 2021

(30) Foreign Application Priority Data

Dec. 25, 2019 (JP) .................................. 2019-234557
Dec. 21, 2020 (JP) .................................. 2020-211391

(51) Int. Cl.
*A61B 6/00* (2024.01)
*A61B 6/03* (2006.01)
(Continued)

(52) U.S. Cl.
CPC ............ *A61B 6/5217* (2013.01); *A61B 6/032* (2013.01); *A61B 6/504* (2013.01); *A61B 6/507* (2013.01);
(Continued)

(58) Field of Classification Search
CPC ....... A61B 6/52; A61B 6/5205; A61B 6/5211; A61B 6/5217; A61B 6/5229;
(Continued)

(56) References Cited

U.S. PATENT DOCUMENTS

2011/0071404 A1* 3/2011 Schmitt .............. A61B 5/02007
 382/128
2014/0086461 A1* 3/2014 Yao ........................ A61B 6/541
 382/128
(Continued)

FOREIGN PATENT DOCUMENTS

| CN | 109166101 A | 1/2019 |
| JP | 2015-167790 A | 9/2015 |
| WO | WO 2019/238754 A1 | 12/2019 |

OTHER PUBLICATIONS

Office Action issued Jun. 5, 2024, in Japanese Patent Application No. 2020-211391 filed Dec. 21, 2020, 4 pages.

*Primary Examiner* — Carolyn A Pehlke
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to obtain medical image data related to a coronary artery of a subject. The processing circuitry is configured to derive a value of a blood flow parameter indicating hemodynamics of the coronary artery, on the basis of the medical image data. The processing circuitry is configured to display information indicating a change in the value of the blood flow parameter along the coronary artery, by using a graph of which the vertical axis expresses values of the blood flow parameter and of which the horizontal axis corresponds to the distance direction along the coronary artery and is configured to further display supplementary information indicating the structure of the coronary artery together with the graph.

20 Claims, 18 Drawing Sheets

(51) Int. Cl.
*A61B 6/50* (2024.01)
*G06T 7/00* (2017.01)
*G06T 11/20* (2006.01)

(52) U.S. Cl.
CPC .......... *G06T 7/0012* (2013.01); *G06T 7/0016* (2013.01); *G06T 11/206* (2013.01); *G06T 2207/10081* (2013.01); *G06T 2207/30048* (2013.01); *G06T 2207/30104* (2013.01)

(58) Field of Classification Search
CPC ......... A61B 6/5294; A61B 8/06; A61B 8/065; A61B 8/085; A61B 8/0883; A61B 8/0891; A61B 8/12; A61B 8/46; A61B 8/461; A61B 8/463; A61B 8/465; A61B 8/52; A61B 8/5215; A61B 8/5223; G06T 7/0012; G06T 7/0016; G06T 2207/10081; G06T 2207/10072; G06T 2207/10116; G06T 2207/10132; G06T 2207/30101; G06T 2207/30104; G06T 2207/30048; G06T 11/206

See application file for complete search history.

(56) References Cited

U.S. PATENT DOCUMENTS

| | | | |
|---|---|---|---|
| 2015/0228115 A1 | 8/2015 | Wakai et al. | |
| 2015/0262357 A1* | 9/2015 | Igarashi | A61B 6/5211 |
| | | | 382/131 |
| 2015/0342537 A1* | 12/2015 | Taylor | A61B 5/026 |
| | | | 600/508 |
| 2017/0032097 A1 | 2/2017 | Itu et al. | |
| 2018/0243033 A1* | 8/2018 | Tran | G16H 30/20 |
| 2019/0209114 A1 | 7/2019 | Nishioka et al. | |
| 2020/0129142 A1* | 4/2020 | Chao | A61B 8/5223 |
| 2020/0367835 A1* | 11/2020 | Anderson | A61B 5/0215 |

\* cited by examiner

Optional marker of area position

Optional marker of area position

FIG.18
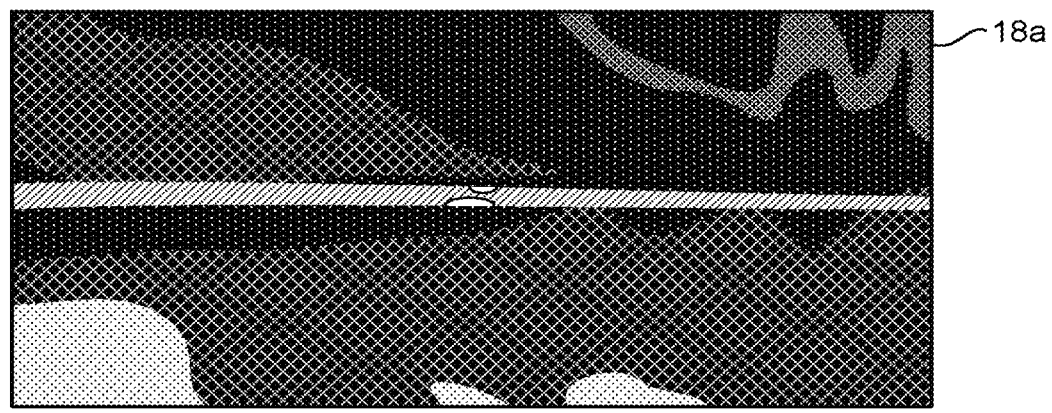
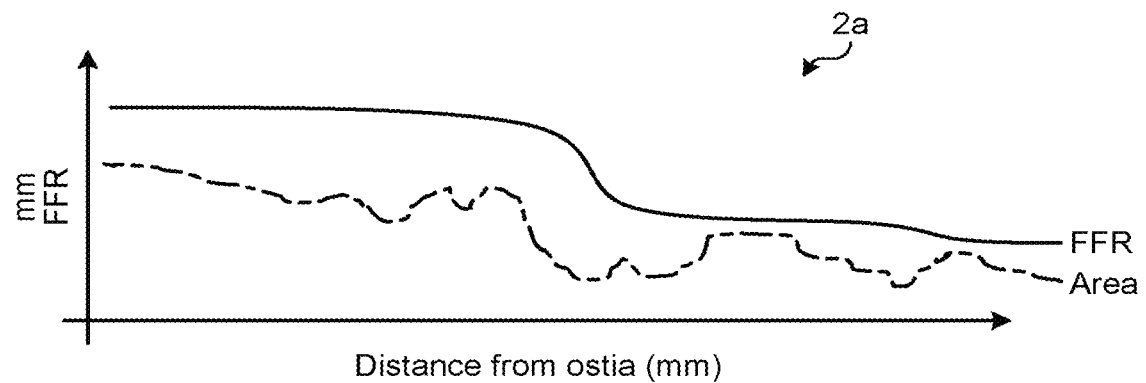

MEDICAL IMAGE PROCESSING APPARATUS, RECORDING MEDIUM, AND SYSTEM

CROSS-REFERENCE TO RELATED APPLICATIONS

This application is based upon and claims the benefit of priority from Japanese Patent Application No. 2019-234557, filed on Dec. 25, 2019, and Japanese Patent Application No. 2020-211391, filed on Dec. 21, 2020; the entire contents of which are incorporated herein by reference.

FIELD

Embodiments disclosed in the present specification and the accompanying drawings relate generally to a medical image processing apparatus, a recording medium, and a system.

BACKGROUND

Conventionally, a technique is known by which, on the basis of medical image data generated by a medical image diagnosis apparatus such as an X-ray Computed Tomography (CT) apparatus, a value of a blood flow parameter expressing hemodynamics of a coronary artery is derived. Generally speaking, to determine relevance between the morphology of a coronary artery and such blood flow parameter and whether or not treatment is required on the basis of values of the blood flow parameter, it is necessary to understand which part of the actual coronary artery corresponds to the position from which the value of the blood flow parameter was derived.

BRIEF DESCRIPTION OF THE DRAWINGS

FIG. 18 is a chart illustrating an example of information displayed by a display controlling function according to a sixteenth modification example;

DETAILED DESCRIPTION

A medical image processing apparatus according to an embodiment includes an obtaining unit, an analyzing unit, and a display controlling unit. The obtaining unit is configured to obtain medical image data related to a coronary artery of a subject. The analyzing unit is configured to derive a value of a blood flow parameter indicating hemodynamics of the coronary artery, on the basis of the medical image data. The display controlling unit is configured to display information indicating a change in the value of the blood flow parameter along the coronary artery, by using a graph of which the vertical axis expresses values of the blood flow parameter and of which the horizontal axis corresponds to the distance direction along the coronary artery and is configured to further display supplementary information indicating the structure of the coronary artery together with the graph.

Embodiments of a medical image processing apparatus, a recording medium and a system will be explained below, with reference to the accompanying drawings.

In the embodiments below, examples will be explained in which CT image data generated by an X-ray CT apparatus is used as the medical image data.

First Embodiment

Figure 1:
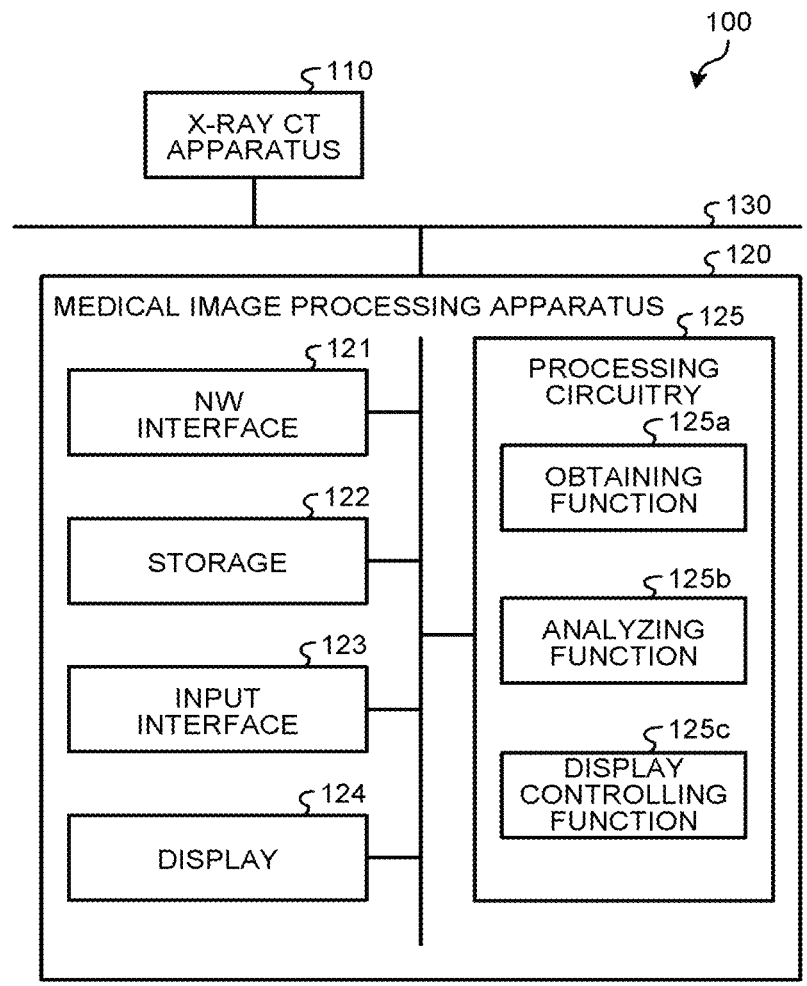
FIG. 1 is a diagram illustrating an exemplary configuration of a medical image processing system according to a first embodiment.

FIG. 1 is a diagram illustrating an exemplary configuration of a medical image processing system according to a first embodiment.

For example, as illustrated in FIG. 1, a medical image processing system 100 according to the present embodiment includes an X-ray CT apparatus 110 and a medical image processing apparatus 120. In this situation, the apparatuses are communicably connected to each other via a network 130.

The X-ray CT apparatus 110 is configured to generate CT image data related to a subject. More specifically, the X-ray CT apparatus 110 is configured to acquire projection data by detecting X-rays that have passed through the subject, while moving and rotating an X-ray tube and an X-ray detector that are substantially centered on the subject. Further, on the basis of the acquired projection data, the X-ray CT apparatus 110 is configured to generate the CT image data.

The medical image processing apparatus 120 is configured to obtain the CT image data from the X-ray CT apparatus 110 via the network 130 and to perform various types of image processing processes on the basis of the obtained CT image data. For example, the medical image processing apparatus 120 is realized by using a computer device such as a server, a workstation, a personal computer, or the like.

Further, on the basis of the CT image data related to a coronary artery of the subject, the medical image processing apparatus 120 is configured to derive values of a blood flow parameter indicating hemodynamics of the coronary artery.

Generally speaking, to determine relevance between the morphology of a coronary artery and such blood flow parameter and whether or not treatment is required on the basis of values of the blood flow parameter, it is necessary to understand which part of the actual coronary artery corresponds to the position from which the value of the blood flow parameter was derived.

Accordingly, in the present embodiment, the medical image processing apparatus 120 is configured to display information indicating changes in values of the blood flow parameter along the coronary artery, by using a graph of which the vertical axis expresses the values of the blood flow parameter and of which the horizontal axis corresponds to the distance direction along the coronary artery and is configured to further display supplementary information indicating the structure of the coronary artery, together with the graph.

In this configuration, because the supplementary information indicating the structure of the coronary artery is displayed together with the graph indicating the changes in values of the blood flow parameter, it is possible to easily understand a correspondence relationship between the positions from which the values of the blood flow parameter were derived and the positions in the coronary artery.

Next, a configuration of the medical image processing apparatus 120 described above will be explained in detail.

For example, as illustrated in FIG. 1, the medical image processing apparatus 120 includes a network (NW) interface 121, storage 122, an input interface 123, a display 124, and processing circuitry 125.

The NW interface 121 is connected to the processing circuitry 125 and is configured to control data communication with other devices performed via the network 130. More specifically, under control of the processing circuitry 125, the NW interface 121 is configured to control transmission and reception of various types of data performed between the other devices and the system. For example, the NW interface 121 is realized by using a network card, a network adaptor, a Network Interface Controller (NIC), or the like.

The storage 122 is connected to the processing circuitry 125 and is configured to store therein various types of data. More specifically, under the control of the processing circuitry 125, the storage 122 is configured to store therein various types of data and to read and update the stored data. For example, the storage 122 is realized by using a semiconductor memory element such as a Random Access Memory (RAM) or a flash memory, or a hard disk, an optical disk, or the like.

The input interface 123 is connected to the processing circuitry 125 and is configured to receive operations to input various types of instructions and various types of information, from an operator. More specifically, the input interface 123 is configured to convert the input operations received from the operator into electrical signals and to output the electrical signals to the processing circuitry 125. For example, the input interface 123 is realized by using a trackball, a switch button, a mouse, a keyboard, a touchpad on which input operations are performed by touching the operation surface thereof, a touch screen in which a display screen and a touchpad are integrally formed, a contactless input circuit using an optical sensor, an audio input circuit using a microphone, and/or the like. In the present disclosure, the input interface 123 does not necessarily have to include one or more physical operation component parts such as a mouse, a keyboard, and/or the like. For instance, possible examples of the input interface 123 include electrical signal processing circuitry configured to receive an electrical signal corresponding to an input operation from an external input device provided separately from the apparatus and to output the electrical signal to controlling circuitry.

The display 124 is connected to the processing circuitry 125 and is configured to display various types of information and various types of data. More specifically, under the control of the processing circuitry 125, the display 124 is configured to convert the various types of information and the various types of data into display-purpose electrical signals and to output the electrical signals. For example, the display 124 is realized by using a Liquid Crystal Display (LCD) device, a touch panel, or the like.

The processing circuitry 125 is configured to control operations of the medical image processing apparatus 120 in accordance with the input operations received from the operator via the input interface 123.

More specifically, the processing circuitry 125 includes an obtaining function 125a, an analyzing function 125b, and a display controlling function 125c. The obtaining function 125a is an example of the obtaining unit. The analyzing function 125b is an example of the analyzing unit. The display controlling function 125c is an example of the display controlling unit.

The obtaining function 125a is configured to obtain the CT image data related to the coronary artery of the subject. More specifically, via the network 130, the obtaining function 125a is configured to obtain the CT image data from the X-ray CT apparatus 110. Further, the obtaining function 125a is configured to store the obtained CT image data into the storage 122.

The analyzing function 125b is configured to derive values of the blood flow parameter indicating hemodynamics of the coronary artery, on the basis of the CT image data obtained by the obtaining function 125a.

More specifically, the analyzing function 125b is configured to read the CT image data obtained by the obtaining function 125a from the storage 122 and to derive the values of the blood flow parameter on the basis of the read CT image data.

In this situation, as the blood flow parameter, it is possible to use any of various types of publicly-known parameters.

For example, as the values of the blood flow parameter, the analyzing function 125b may derive values of a pressure parameter such as a Fractional Flow Reserve (FFR) value, an instantaneous wave-Free Ratio (iFR), or a Quantitative Flow Ratio (QFR) or may derive a flow rate, a pressure ratio, vorticity, kinetic energy, turbulence intensity, shear stress, or the like. Alternatively, for example, as the values of the blood flow parameter, the analyzing function 125b may derive a gradient of any one of the value of these parameters. In this situation, the derived gradient may be a gradient with respect to the distance direction along the coronary artery, or a gradient with respect to other arbitrary direction.

Further, as the method for deriving the blood flow parameter, it is possible to use any of various types of publicly-known methods. For example, the analyzing function 125b may derive the blood flow parameter by performing a simulation calculation while using a publicly-known fluid analysis method. Alternatively, for example, the analyzing function 125b may derive the blood flow parameter by using a trained model configured to receive an input of CT image data related to a coronary artery and to output the blood flow parameter related to the coronary artery. In that situation, for example, the trained model is generated, in advance, through machine learning that uses CT image data related to coronary arteries and the blood flow parameter expressing hemodynamics of the coronary arteries as learning-purpose data and is stored into the storage 122. In this situation, as the method of the machine learning, it is possible to use any of various types of methods such as deep learning, a non-linear discriminant analysis, a support vector machine, a random forest, a naïve Bayes scheme, or the like.

Further, on the basis of the CT image data, the analyzing function 125b is configured to derive values of a morphological parameter indicating a morphology of the coronary artery.

More specifically, the analyzing function 125b is configured to read the CT image data obtained by the obtaining function 125a from the storage 122 and to derive the values of the morphological parameter on the basis of the read CT image data.

In this situation, as the morphological parameter also, it is possible to use any of various types of publicly-known parameters. For example, as the values of the morphological parameter, the analyzing function 125b may derive values of a blood vessel cross-sectional area or a blood vessel lumen diameter or may derive values of a stenosis rate or a ratio of a blood vessel cross-sectional area to a reference cross-sectional area. Further, for example, as the values of the morphological parameter, the analyzing function 125b may derive values of eccentricity index, vessel wall measurements (for example, lumen contour or wall contour), remodeling index, or cross sectional plaque burden, etc.

Further, as the method for deriving the morphological parameter also, it is possible to use any of various types of publicly-known methods. For example, the analyzing function 125b may derive the morphological parameter by using a publicly-known image analysis method. Alternatively, for example, the analyzing function 125b may derive the morphological parameter by using a trained model configured to receive an input of CT image data related to a coronary artery and to output the morphological parameter related to the coronary artery. In that situation, for example, the trained model is generated, in advance, through machine learning that uses CT image data related to coronary arteries and the morphological parameter expressing morphologies of the coronary arteries as learning-purpose data and is stored into the storage 122. In this situation, as the method of the machine learning, it is possible to use any of various types of methods such as deep learning, a non-linear discriminant analysis, a support vector machine, a random forest, a naïve Bayes scheme, or the like.

The display controlling function 125c is configured to display information indicating changes in values along the coronary artery with respect to the blood flow parameter derived by the analyzing function 125b, by using a graph of which the vertical axis expresses the values of the blood flow parameter and of which the horizontal axis corresponds to the distance direction along the coronary artery and is configured to further display the supplementary information indicating the structure of the coronary artery together with the graph.

More specifically, the display controlling function 125c is configured to cause the display 124 to display the graph indicating the changes in values along the coronary artery with respect to the blood flow parameter derived by the analyzing function 125b and the supplementary information indicating the structure of the coronary artery.

In the present embodiment, as the supplementary information indicating the structure of the coronary artery, the display controlling function 125c is configured to further display, in the graph, information indicating changes in values of the morphological parameter along the coronary artery.

For example, as the supplementary information indicating the structure of the coronary artery, the display controlling function 125c is configured to further display, in a graph, information indicating changes in the blood vessel cross-sectional area.

Figure 2:
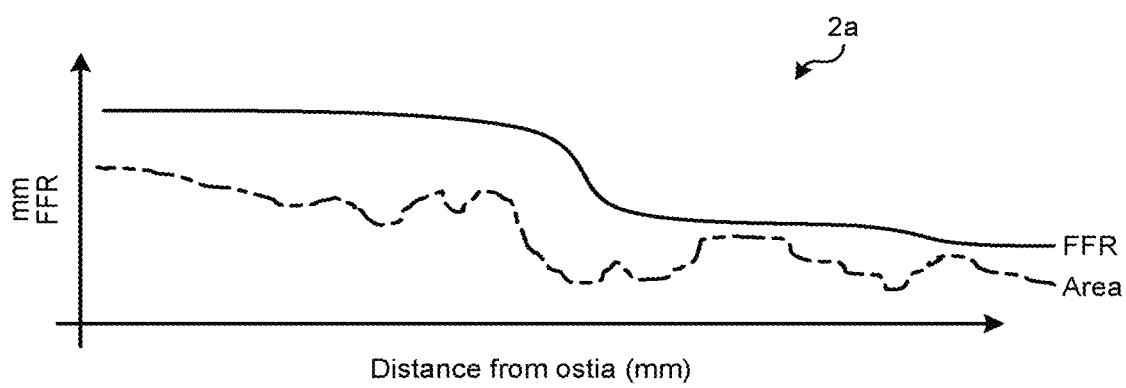
FIG. 2 is a chart illustrating an example of information displayed by a display controlling function according to the first embodiment.

FIG. 2 is a chart illustrating an example of the information displayed by the display controlling function 125c according to the first embodiment.

For example, as illustrated in FIG. 2, with respect to a section of the coronary artery selected by the operator, the display controlling function 125c is configured to display a curve indicating changes in FFR, by using a graph 2a of which the vertical axis expresses values of FFR and of which the horizontal axis expresses distance from the ostium of the coronary artery.

Further, for example, as the supplementary information indicating the structure of the coronary artery in this section, the display controlling function 125c is configured to further display, in the graph 2a, a curve indicating changes in the blood vessel cross-sectional area (Area [mm]) along the coronary artery.

In the display configured in this manner, because the changes in FFR and the changes in the blood vessel cross-sectional area along the coronary artery are displayed in the single graph (i.e., the graph 2a), it is possible to easily understand the correlation between FFR and the blood vessel cross-sectional area in each of the different positions in the coronary artery.

In this situation, for example, the processing circuitry 125 is realized by using a processor. In that situation, each of the processing functions of the processing circuitry 125 is stored in the storage 122 in the form of a computer-executable program. Further, the processing circuitry 125 is configured to realize the processing functions corresponding to the programs, by reading and executing the programs from the storage 122. In other words, when having read the programs, the processing circuitry 125 has the processing functions illustrated in FIG. 1.

Figure 3:
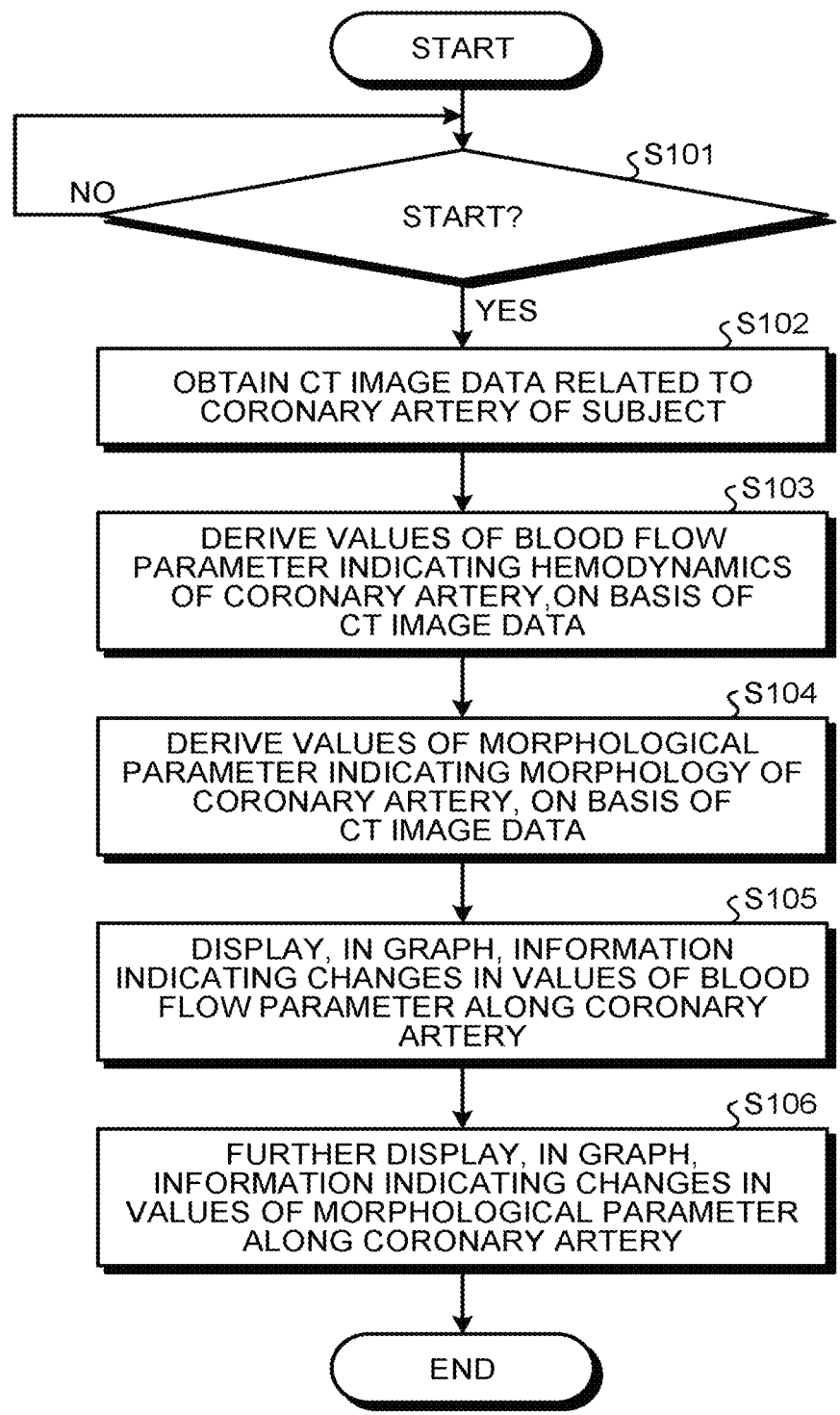
FIG. 3 is a flowchart illustrating a processing procedure in a process performed by a medical image processing apparatus according to the first embodiment.

FIG. 3 is a flowchart illustrating a processing procedure in a process performed by the medical image processing apparatus 120 according to the first embodiment.

For example, as illustrated in FIG. 3, in the present embodiment, upon receipt of an instruction to start the process from the operator via the input interface 123 (step S101: Yes), the obtaining function 125a obtains CT image data related to a coronary artery of the subject (step S102).

The processes at steps S101 and S102 are realized, for example, as a result of the processing circuitry 125 reading and executing the program corresponding to the obtaining function 125a from the storage 122.

Subsequently, the analyzing function 125b reads the CT image data obtained by the obtaining function 125a from the storage 122 and derives the values of the blood flow parameter indicating hemodynamics of the coronary artery on the basis of the read CT image data (step S103). Further, on the basis of the CT image data read from the storage 122, the analyzing function 125b derives the values of the morphological parameter indicating the morphology of the coronary artery (step S104).

The processes at steps S103 and S104 are realized, for example, as a result of the processing circuitry 125 reading and executing the program corresponding to the analyzing function 125b from the storage 122.

After that, the display controlling function 125c displays the information indicating the changes in values along the coronary artery with respect to the blood flow parameter derived by the analyzing function 125b, by using a graph (step S105). Further, the display controlling function 125c causes the display 124 to further display, in the graph, the information indicating the changes in values along the coronary artery with respect to the morphological parameter derived by the analyzing function 125b (step S106).

The processes at steps S105 and S106 are realized, for example, as a result of the processing circuitry 125 reading and executing the program corresponding to the display controlling function 125c from the storage 122.

As explained above, in the first embodiment, the display controlling function 125c is configured to display the information indicating the changes in values of the blood flow parameter along the coronary artery, by using the graph of which the vertical axis expresses the values of the blood flow parameter and of which the horizontal axis corresponds to the distance direction along the coronary artery and is configured to further display the supplementary information indicating the structure of the coronary artery together with the graph. With this configuration, by referring to the supplementary information together with the graph, it is possible to easily understand the correspondence relationship between the positions from which the values of the blood flow parameter were derived and the positions in the coronary artery. Consequently, it is possible to easily formulate a treatment plan.

Further, for example, in the first embodiment, the display controlling function 125c is configured to further display, in the graph, the information indicating the changes in values of the morphological parameter along the coronary artery, as the supplementary information indicating the structure of the coronary artery. With this configuration, it is possible to easily understand the correlation between the values of the blood flow parameter in the different positions in the coronary artery and the morphology of the blood vessel.

For example, with the coronary arteries, there may be some situations where the form and hemodynamics do not correspond to each other, e.g., "FFR has not decreased although the coronary artery apparently has a stenosis".

Thus, to determine a treatment plan, it is important to observe not only a distribution of FFR values, but also a correlation between FFR values and the morphology of the blood vessel. In this regard, for example, when an image of the coronary artery was displayed together with a graph indicating changes in FFR, because the morphology of the blood vessel would have to be visually read from the image, it might be difficult in some situations to understand the relevance between the form and the FFR values in different positions in the coronary artery. In contrast, in the first embodiment, for example, the changes in FFR and the changes in the blood vessel cross-sectional area along the coronary artery are displayed in the one graph. It is therefore possible to easily understand the correlation between the FFR values and the blood vessel cross-sectional areas in the different positions in the coronary artery.

Further, in the first embodiment described above, the example was explained in which the information indicating the changes in values of the blood flow parameter and the changes in values of the morphological parameter is displayed in the graph. However, possible examples of the information displayed by the display controlling function 125c are not limited to this example. Accordingly, in the following sections, modification examples of the information displayed by the display controlling function 125c will be explained.

FIRST MODIFICATION EXAMPLE

For example, as the supplementary information indicating the structure of the coronary artery, the display controlling function 125c may further display, in the graph, information indicating changes in a stenosis ratio along the coronary artery.

Figure 4:
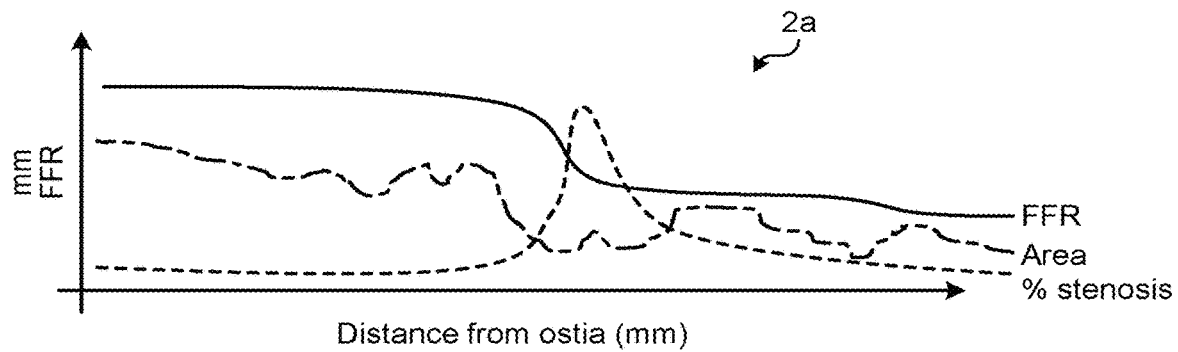
FIG. 4 is a chart illustrating an example of information displayed by a display controlling function according to a first modification example.

FIG. 4 is a chart illustrating an example of information displayed by the display controlling function 125c according to a first modification example.

For instance, as illustrated in FIG. 4, the display controlling function 125c may further display, in the graph 2a, a curve indicating changes in the stenosis ratio (% stenosis) along the coronary artery with respect to the section of the coronary artery, in addition to the information in the example of FIG. 2. In this situation, the stenosis ratio exhibits a larger value in a location where the blood vessel cross-sectional area is locally smaller.

In the display configured in this manner, because the changes in FFR and the stenosis ratios along the coronary artery are displayed in the single graph (i.e., the graph 2a), it is possible to understand, in detail, the relevance between the extent of the stenosis of the coronary artery and decreases in FFR.

SECOND MODIFICATION EXAMPLE

In another example, the display controlling function 125c may further display a color bar in which a color corresponding to the value of the blood flow parameter is assigned to each of the different positions in the distance direction along the coronary artery.

Figure 5:
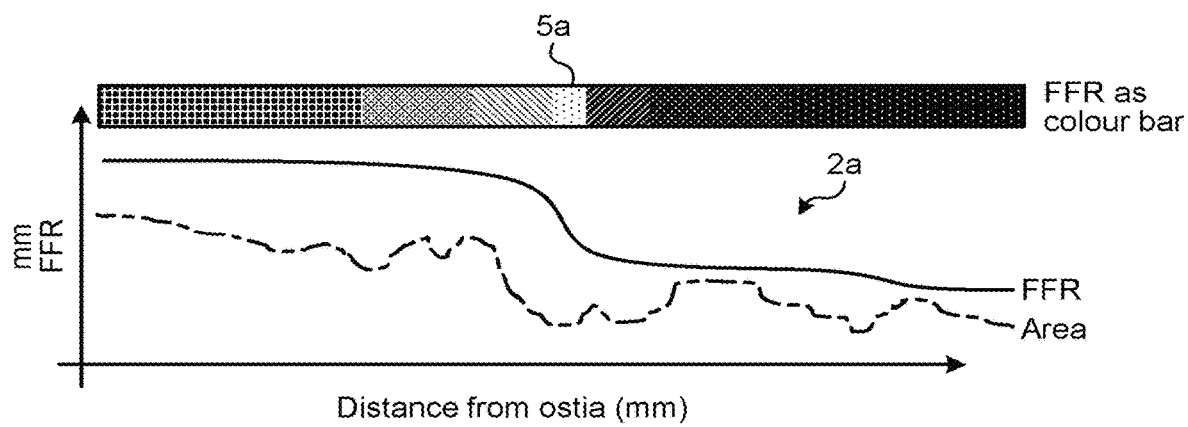
FIG. 5 is a chart illustrating an example of information displayed by a display controlling function according to a second modification example.

FIG. 5 is a chart illustrating an example of information displayed by the display controlling function 125c according to a second modification example.

For instance, as illustrated in FIG. 5, the display controlling function 125c may display, in addition to the information in the example of FIG. 2, a rectangular color bar 5a (FFR as colour bar) in which a color corresponding to the value of FFR is assigned to each of the different positions in the distance direction along the coronary artery. In this situation, for example, the display controlling function 125c may set the length of the color bar 5a so as to match the scale in the distance direction of the horizontal axis of the graph 2a indicating the changes in FFR and in the blood vessel cross-sectional area and may arrange the graph 2a alongside the color bar 5a so that the positions thereof in the distance direction are aligned with each other.

In the display configured in this manner, by further referring to the color bar 5a, it is possible to more easily understand the correlation between FFR and the blood vessel cross-sectional area in each of the different positions in the coronary artery.

THIRD MODIFICATION EXAMPLE

In yet another example, the display controlling function 125c may display a color bar in such a mode that expresses the shape of the coronary artery.

Figure 6:
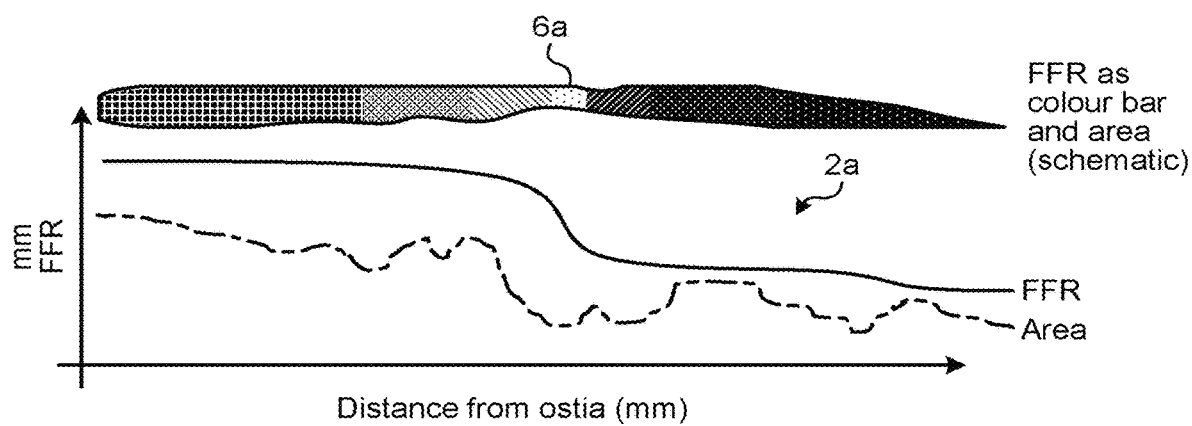
FIG. 6 is a chart illustrating an example of information displayed by a display controlling function according to a third modification example.

FIG. 6 is a chart illustrating an example of information displayed by the display controlling function 125c according to a third modification example.

For instance, as illustrated in FIG. 6, the display controlling function 125c may display, similarly to the example in FIG. 5, a color bar 6a in which a color corresponding to the value of FFR is assigned to each of the different positions in the distance direction along the coronary artery. In this situation, for example, on the basis of the CT image data obtained by the obtaining function 125a, the display controlling function 125c may extract the cross-sectional shapes of the coronary artery in the section and display the color bar 6a shaped to indicate the extracted cross-sectional shapes (FFR as colour bar (schematic)).

In the display configured in this manner, by further referring to the color bar 6a indicating the shape of the coronary artery, it is possible to more intuitively understand the correlation between the FFR values and the blood vessel cross-sectional areas in the different positions in the coronary artery.

FOURTH MODIFICATION EXAMPLE

In yet another example, the display controlling function 125c may further display a tomographic image of the coronary artery along the distance direction and may display a marker indicating the position in the distance direction in each of the corresponding positions in the graph and in the tomographic image.

Figure 7:
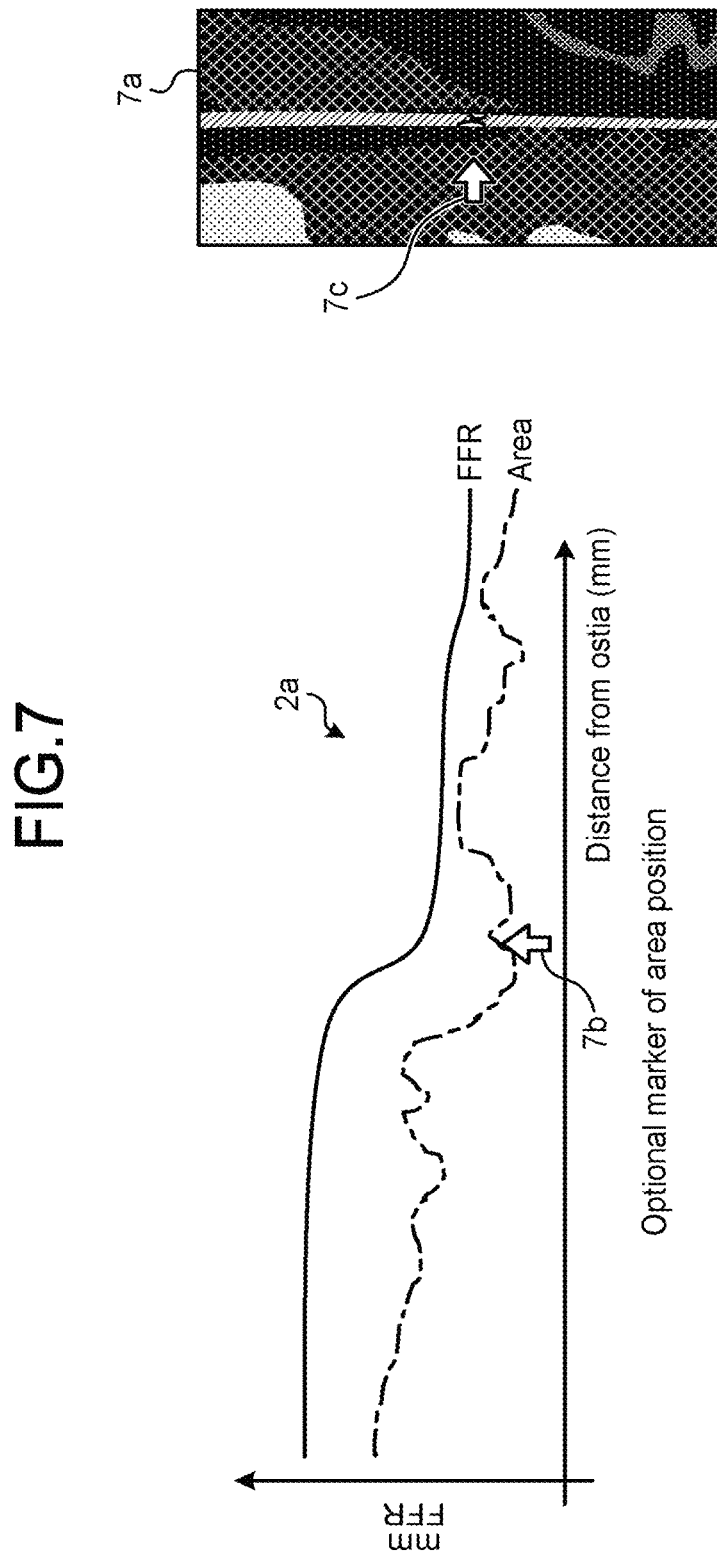
FIG. 7 is a chart illustrating an example of information displayed by a display controlling function according to a fourth modification example.

FIG. 7 is a chart illustrating an example of information displayed by the display controlling function 125c according to a fourth modification example.

For example, as illustrated in FIG. 7, in addition to the information in the example of FIG. 2, the display controlling function 125c may display a Curved Planar Reconstruction (CPR) image 7a of the coronary artery in the section. In this situation, for example, on the basis of the CT image data obtained by the obtaining function 125a, the display controlling function 125c may generate the CPR image 7a in the section and display the generated CPR image 7a so as to be arranged alongside the graph 2a indicating the changes in FFR and in the blood vessel cross-sectional area.

Further, for example, the display controlling function 125c may display a marker (an arrow symbol in FIG. 7) 7b indicating the position in the distance direction along the coronary artery, in the graph 2a indicating the changes in FFR and in the blood vessel cross-sectional area. In this situation, the display controlling function 125c may display the marker 7b on the curve of the cross-sectional area (Optional marker of area position) or may display the marker 7b on the curve of FFR. Also, at the same time, the display controlling function 125c may display, within the CPR image 7a, another marker 7c in such a position that corresponds to the position of the marker 7b displayed in the graph.

In this situation, for example, the display controlling function 125c may receive, from the operator, an operation to move one of the markers 7b and 7c displayed in the graph 2a and in the CPR image 7a, respectively. Further, upon receipt of the operation, the display controlling function 125c moves the other marker to such a position that corresponds to the position of the moved marker. With this arrangement, the display controlling function 125c is configured move the marker 7b displayed in the graph 2a indicating the changes in FFR and in the blood vessel cross-sectional area and the marker 7c displayed in the CPR image 7a in conjunction with each other so as to indicate mutually the same position in the distance direction.

In the display configured in this manner, by referring to the markers 7b and 7c displayed in the graph 2a and in the CPR image 7a respectively, it is possible to more easily understand the correspondence relationship between the positions from which the FFR values were derived and the positions in the coronary artery.

FIFTH MODIFICATION EXAMPLE

In yet another example, the display controlling function 125c may further display the supplementary information indicating the structure of the coronary artery, together with the tomographic image.

Figure 8:
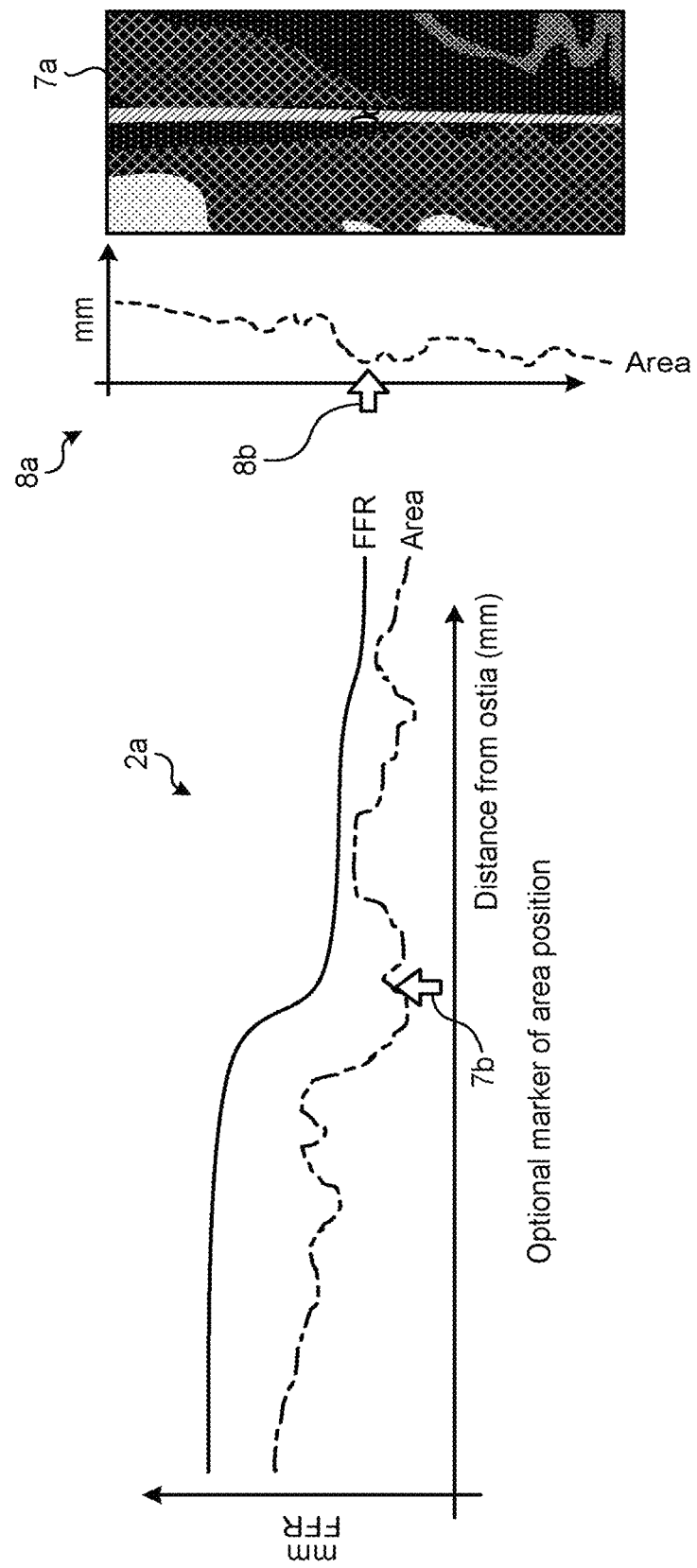
FIG. 8 is a chart illustrating an example of information displayed by a display controlling function according to a fifth modification example.

FIG. 8 is a chart illustrating an example of information displayed by the display controlling function 125c according to a fifth modification example.

For instance, as illustrated in FIG. 8, in addition to the information in the example of FIG. 7, the display controlling function 125c may display, as the supplementary information indicating the structure of the coronary artery, a graph 8a indicating changes in the blood vessel cross-sectional area along the coronary artery, so as to be arranged alongside the CPR image 7a. In this situation, the display controlling function 125c sets the horizontal axis of the graph 8a so as to match the scale in the distance direction of the CPR image 7a and arranges the CPR image 7a alongside the graph 8a so that the positions thereof in the distance direction are aligned with each other.

In this situation, for example, the display controlling function 125c may display, similarly to the example in FIG. 7, the marker 7b indicating the position in the distance direction along the coronary artery in the graph 2a indicating the changes in FFR and in the blood vessel cross-sectional area and may also display another marker 8b in the corresponding position in the graph 8a indicating the blood vessel cross-sectional area and being displayed alongside the CPR image 7a. Further, upon receipt of an operation from the operator to move one of the markers, the display controlling function 125c moves the other marker to such a position that corresponds to the position of the moved marker. With this arrangement, the display controlling function 125c is configured to move the marker 7b displayed in the graph 2a indicating the changes in FFR and in the blood vessel cross-sectional area and the other marker 8b displayed in the graph 8a indicating the cross-sectional areas and being arranged alongside the CPR image 7a, in conjunction with each other so as to indicate mutually the same position in the distance direction.

In the display configured in this manner, by referring to the graph 8a indicating the changes in the blood vessel cross-sectional area together with the CPR image 7a, it is possible to understand, more in detail, the correspondence relationship between the positions from which the FFR values were derived and the positions in the coronary artery.

SIXTH MODIFICATION EXAMPLE

In yet another example, as markers each indicating a position in the distance direction along the coronary artery, the display controlling function 125c may display multiple markers each in the graph indicating the changes in FFR and in the blood vessel cross-sectional area, as well as in the tomographic image of the coronary artery along the distance direction, and may further display values of the blood flow parameter and values of the morphological parameter in the positions where the markers are displayed.

Figure 9:
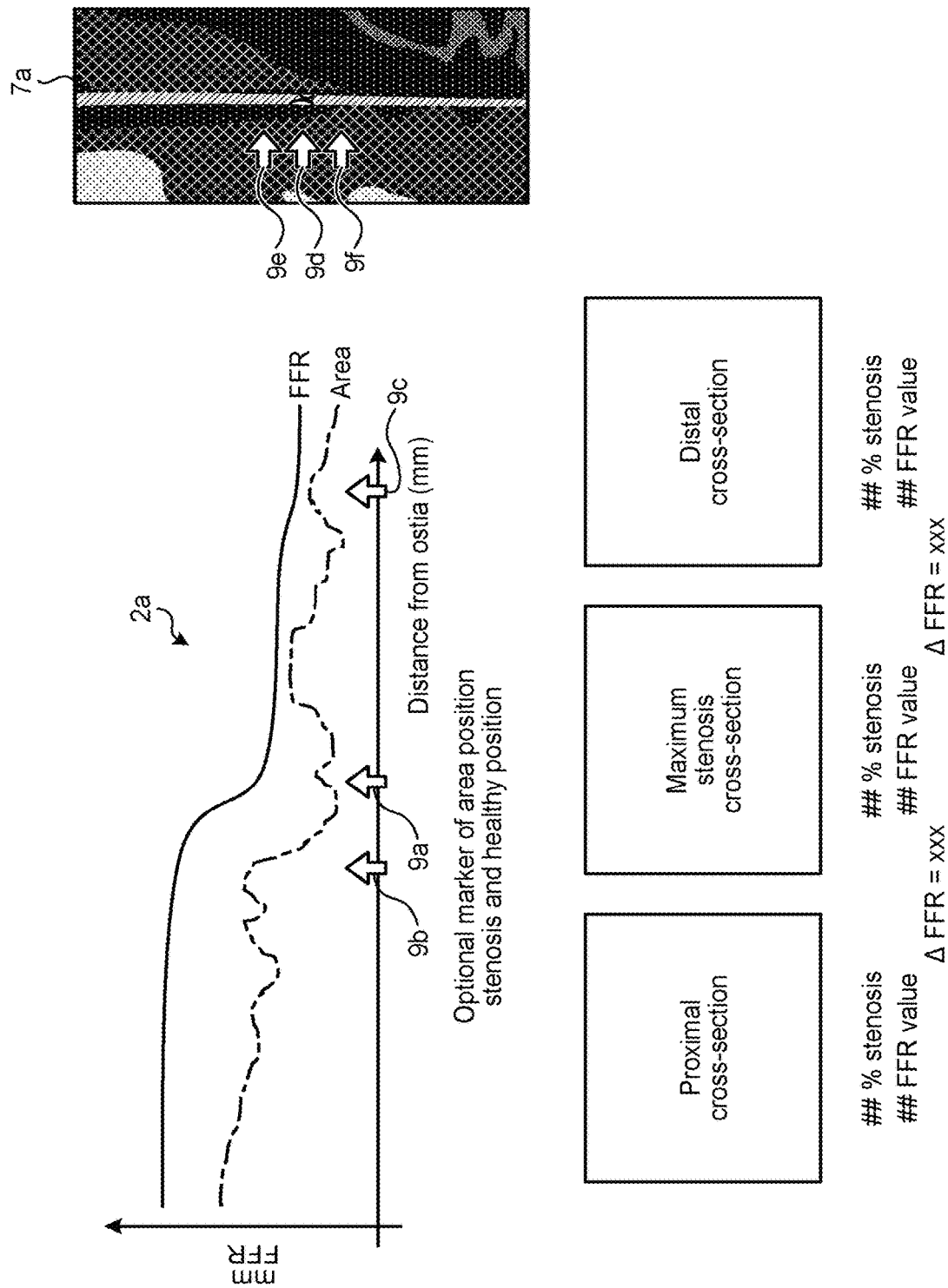
FIG. 9 is a chart illustrating an example of information displayed by a display controlling function according to a sixth modification example.

FIG. 9 is a chart illustrating an example of information displayed by the display controlling function 125c according to a sixth modification example.

For instance, as illustrated in FIG. 9, the display controlling function 125c may display three markers 9a to 9c in the graph 2a illustrated in FIG. 7 and display three markers 9d to 9f in the CPR image 7a illustrated in FIG. 7. In this situation, in the graph 2a and in the CPR image 7a, the display controlling function 125c displays the three markers each, so as to indicate three mutually-different positions in the distance direction along the coronary artery. In this situation, for example, upon receipt of an operation from the operator to move a marker in one selected from between the graph 2a and the CPR image 7a, the display controlling function 125c moves the marker in a corresponding position in the other of the two, in conjunction therewith.

Further, for example, with respect to each of the three positions indicated by the three markers each displayed in the graph 2a and in the CPR image 7a, the display controlling function 125c displays a value of the cross-sectional area, the stenosis ratio (% stenosis), and the FFR value in the position. Further, for example, with respect to each pair of the adjacent markers, the display controlling function 125c displays a delta of FFR (Δ FFR=xxx) between the positions indicated by the adjacent markers. In this situation, for example, the display controlling function 125c may further display a cross-sectional image of each of the positions indicated by the markers.

For example, in the graph 2a, the display controlling function 125c displays the first marker 9a in a position designated by the operator, displays the second marker 9b in a position away from the position of the first marker 9a by a predetermined distance (e.g., 5 mm) toward the upstream side of the coronary artery, and displays the third marker 9c in a position away from the position of the first marker 9a by a predetermined distance (e.g., 5 mm) toward the downstream side of the coronary artery. Further, in the CPR image 7a also, the display controlling function 125c displays the three markers 9d to 9f in such positions that correspond to the positions of the three markers 9a to 9c displayed in the graph 2a.

In another example, in the graph 2a, the display controlling function 125c may display, the first marker 9a in a position having the largest stenosis ratio of the coronary artery (Maximum stenosis cross-section), display the second marker 9b in a position away from the position of the first marker 9a by a predetermined distance toward the upstream side of the coronary artery (Proximal cross-section), and display the third marker 9c in a position away from the position of the first marker 9a toward the downstream side of the coronary artery while being closest to the distal end (Distal cross-section). Further, in the CPR image 7a also, the display controlling function 125c displays the three markers 9d to 9f in such positions that correspond to the positions of the three markers 9a to 9c displayed in the graph 2a.

In the present example, for instance, it is possible to understand the degree of impact of the stenosis, by comparing the FFR value in the position of the first marker 9a with the FFR value in the position of the second marker 9b. Further, it is also possible to judge whether or not there is a stenosis having a bad impact other than the stenosis in the position of the first marker 9a, by comparing the FFR value in the position of the first marker 9a with the FFR value in the position of the third marker 9c.

In the above description, the example was explained in which the display controlling function 125c displays the three markers each in the graph 2a and in the CPR image 7a; however, the present modification example is not limited to this example. For instance, the display controlling function 125c may display four markers or more than four markers each in the graph 2a and in the CPR image 7a.

In the display configured in this manner, it is possible to easily understand the impacts of the stenoses occurring in the coronary artery by using the plurality of markers.

SEVENTH MODIFICATION EXAMPLE

Further, in the first embodiment above, the example was explained in which the supplementary information indicating the structure of the coronary artery is displayed together with the graph indicating the changes in values of the blood flow parameter. In yet another example, it is also acceptable to display information indicating segments of the coronary artery, in place of the supplementary information indicating the structure of the coronary artery.

In that situation, the display controlling function 125c displays the information indicating the changes in values along the coronary artery with respect to the blood flow parameter derived by the analyzing function 125b, by using the graph of which the vertical axis expresses the values of the blood flow parameter and of which the horizontal axis corresponds to the distance direction along the coronary artery and further displays the information indicating the segments of the coronary artery on the horizontal axis of the graph.

Figure 10:
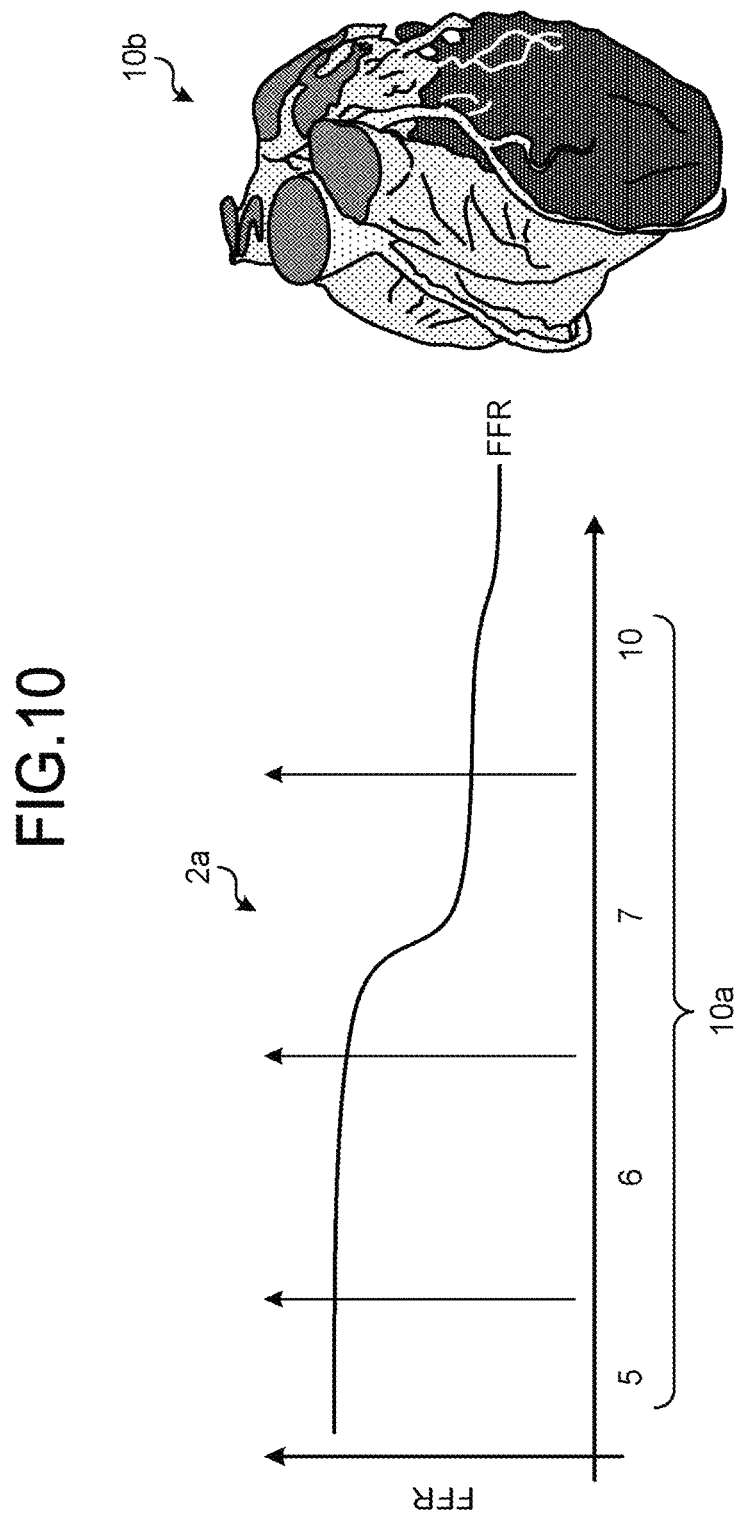
FIG. 10 is a chart illustrating an example of information displayed by a display controlling function according to a seventh modification example.

FIG. 10 is a chart illustrating an example of information displayed by the display controlling function 125c according to a seventh modification example.

For instance, as illustrated in FIG. 10, the display controlling function 125c may display a curve indicating changes in FFR along the coronary artery with respect to one section of the coronary artery selected by the operator, by using the graph 2a of which the vertical axis expresses FFR and of which the horizontal axis expresses distance from the ostium of the coronary artery.

Further, for example, as the information indicating the segments of the coronary artery in the selected section, the display controlling function 125c further displays numerals ("5", "6", "7", and "10", in FIG. 10) 10a indicating the segments of the coronary artery on the horizontal axis of the graph 2a.

In this situation, for example, the display controlling function 125c uses the numerals "1" to "15" indicating the segments of the coronary artery classified by the American Heart Association (AHA) as presented below:

1: From the basal end of the Right Coronary Artery (RCA) to the Right Ventricular Branch (RVB);

2: From the Right Ventricular Branch (RVB) to the Acute Marginal Branch (AM);

3: From the Acute Marginal Branch (AM) to the Posterior Descending (PD);

4: The Atrio-Ventricular (AV) and the Posterior Descending (PD);

5: The Left Main Trunk (LMT);

6: From the Left Main Trunk (LMT) to the first Septal Branch (SB);

7: From the first Septal Branch (SB) to the Second Diagonal branch (D2);

8: From the Second Diagonal branch (D2) to the distal end of the Left Anterior Descending (LAD);

9: The First Diagonal branch (D1);

10: The Second Diagonal branch (D2);

11: From the Left Main Trunk (LMT) to the Obtuse Marginal (OM);

12: The Obtuse Marginal (OM);

13: From the Obtuse marginal (OM) to the Posterior Lateral (PL);

14: The Posterior Lateral (PL);

15: The Posterior Descending (PD).

Further, for example, the display controlling function 125c displays a three-dimensional image (a volume image) 10b obtained by imaging the heart of the subject alongside the graph 2a. In this situation, for example, on the basis of the CT image data obtained by the obtaining function 125a, the display controlling function 125c generates the three-dimensional image 10b obtained by imaging the heart of the subject.

In the display configured in this manner, by referring to the information of the segments with which medical doctors and the like are generally familiar, it is possible to easily understand spatial positions in the coronary artery.

EIGHTH MODIFICATION EXAMPLE

Figure 11:
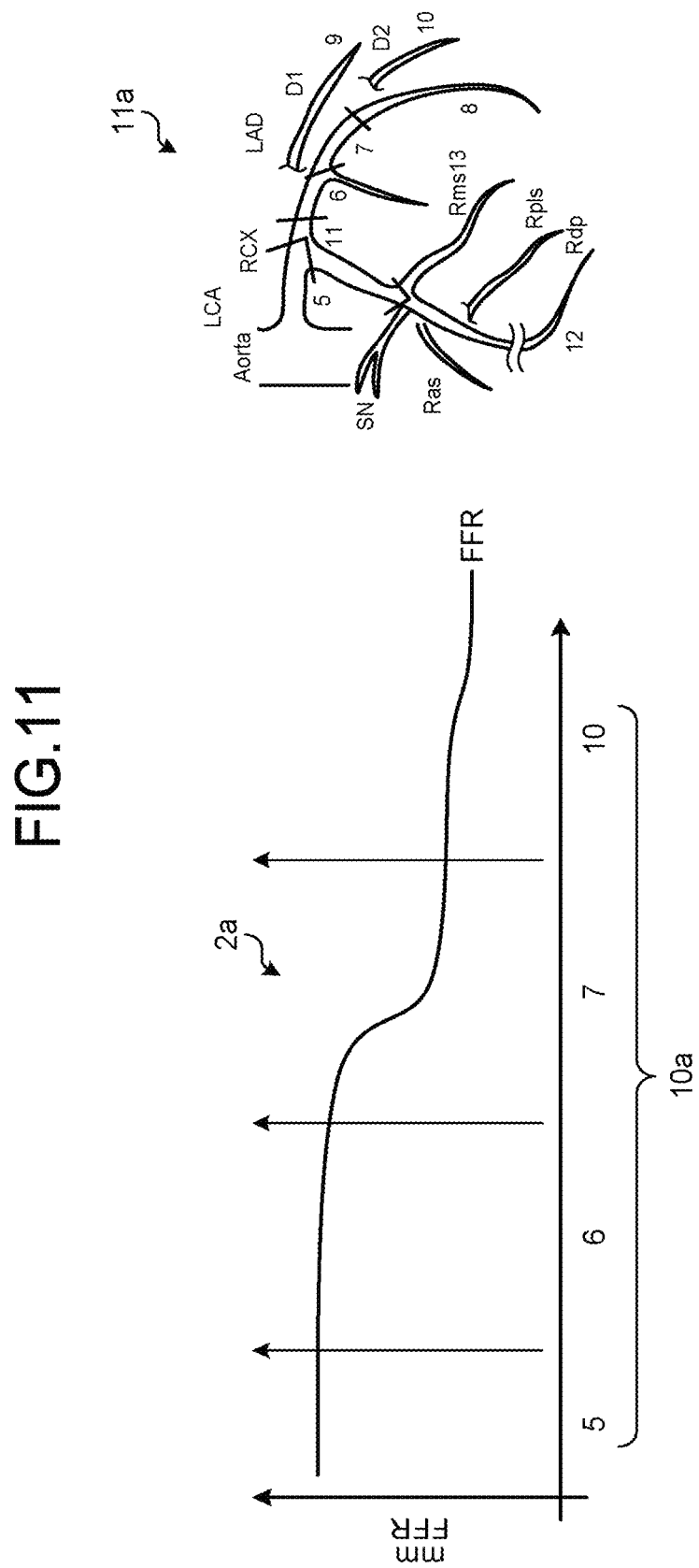
FIG. 11 is a chart illustrating an example of information displayed by a display controlling function according to an eighth modification example.

FIG. 11 is a chart illustrating an example of information displayed by the display controlling function 125c according to an eighth modification example.

In yet another example, as illustrated in FIG. 11, the display controlling function 125c may display an image 11a indicating the positions of the segments in a standard schematic drawing of the heart arranged alongside the graph 2a, in place of the three-dimensional image 10b.

In the display configured in this manner, by further referring to the schematic drawing of the heart indicating the positions of the segments, it is possible to more intuitively understand spatial positions in the coronary artery.

NINTH MODIFICATION EXAMPLE

Further, in the first embodiment above, the example was explained in which the color bar in which the color corresponding to the value of the blood flow parameter is assigned to each of the different positions in the distance direction along the coronary artery is displayed, together with the graph indicating the changes in the blood flow parameter. Alternatively, for example, it is also acceptable to display a tomographic image of the coronary artery along the distance direction, in place of the graph.

Figure 12:
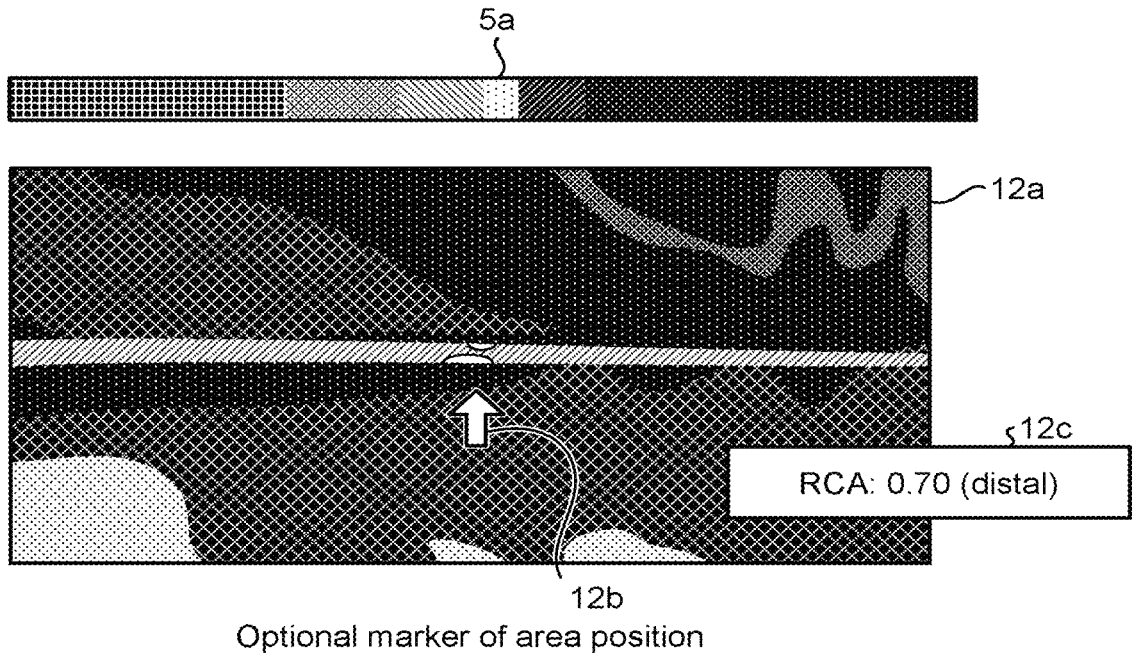
FIG. 12 is a chart illustrating an example of information displayed by a display controlling function according to a ninth modification example.

FIG. 12 is a chart illustrating an example of information displayed by the display controlling function 125c according to a ninth modification example.

For instance, as illustrated in FIG. 12, the display controlling function 125c may display a CPR image 12a of the coronary artery with respect to one section of the coronary artery selected by the operator. In that situation, for example, the display controlling function 125c generates the CPR image 12a of the section on the basis of the CT image data obtained by the obtaining function 125a.

Further, similarly to the example in FIG. 5, the display controlling function 125c may display the rectangular color bar 5a in which the color corresponding to the value of FFR is assigned to each of the different positions in the distance direction along the coronary artery. In that situation, for example, the display controlling function 125c sets the length of the color bar 5a so as to match the scale in the distance direction of the CPR image 12a and arranges the CPR image 12a alongside the color bar 5a so that the positions thereof in the distance direction are aligned with each other.

Further, within the CPR image 12a, the display controlling function 125c displays a marker 12b in a position designated by the operator and displays an FFR value 12c in the position where the marker 12b is displayed.

In the display configured in this manner, it is possible to easily understand the correlation between the FFR values and the blood vessel cross-sectional areas in the different positions in the coronary artery, by comparing the color bar 5a with the CPR image 12a.

TENTH MODIFICATION EXAMPLE

Figure 13:
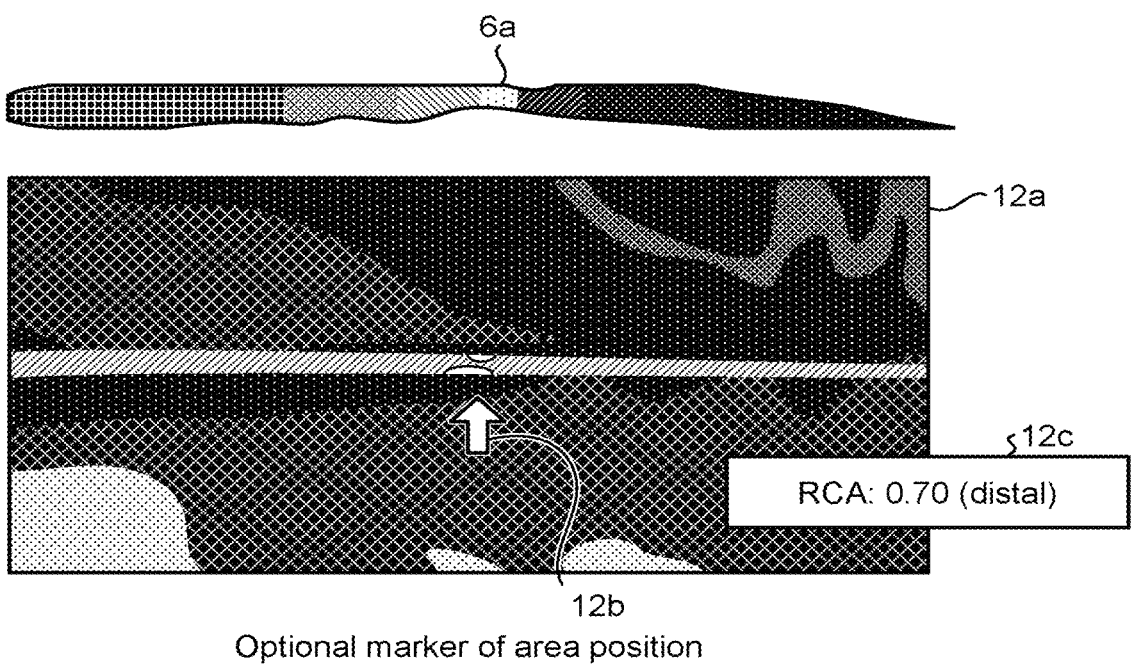
FIG. 13 is a chart illustrating an example of information displayed by a display controlling function according to a tenth modification example.

FIG. 13 is a chart illustrating an example of information displayed by the display controlling function 125c according to a tenth modification example.

In yet another example, as illustrated in FIG. 13, similarly to the example in FIG. 6, the display controlling function 125c may display the color bar 6a shaped to indicate the cross-sectional shapes of the coronary artery, in place of the rectangular color bar 5a.

In the display configured in this manner, it is possible to more intuitively understand the correlation between the FFR values and the blood vessel cross-sectional areas in the different positions in the coronary artery, by comparing the color bar 6a indicating the shape of the coronary artery with the CPR image 12a.

ELEVENT MODIFICATION EXAMPLE

Further, the information displayed by the display controlling function 125c in the first embodiment and the modification examples above may be displayed in combination as appropriate.

Figure 14:
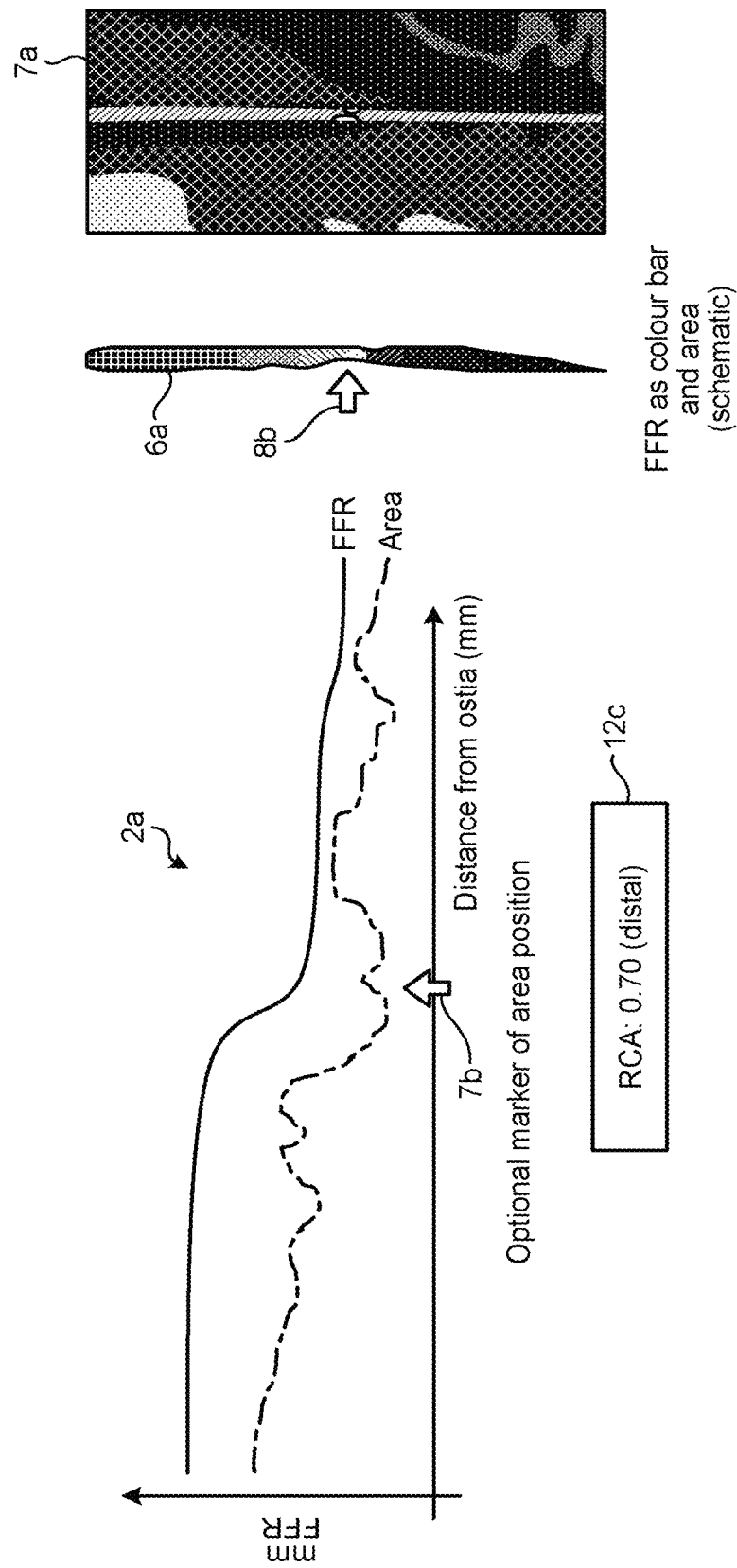
FIG. 14 is a chart illustrating an example of information displayed by a display controlling function according to an eleventh modification example.

FIG. 14 is a chart illustrating an example of information displayed by the display controlling function 125c according to an eleventh modification example.

For instance, as illustrated in FIG. 14, the display controlling function 125c may display, similarly to the example in FIG. 8, the graph 2a indicating the changes in FFR and in the blood vessel cross-sectional area with the CPR image 7a of the coronary artery and may also display the color bar 6a illustrated in FIG. 6 alongside the CPR image 7a, in place of the graph 8a indicating the changes in the blood vessel cross-sectional area. In that situation, for example, the display controlling function 125c sets the length of the color bar 6a so as to match the scale in the distance direction of the CPR image 7a and arranges the CPR image 7a alongside the color bar 6a so that the positions thereof in the distance direction are aligned with each other.

Further, for example, similarly to the example in FIG. 8, the display controlling function 125*c* displays the marker 7*b* in the graph 2*a* indicating the changes in FFR and in the blood vessel cross-sectional area and also displays the marker 8*b* in a corresponding position on the color bar 6*a*. Further, similarly to the example in FIG. 8, the display controlling function 125*c* moves the marker 7*b* displayed in the graph 2*a* and the marker 8*b* displayed on the color bar 6*a* in conjunction with each other so as to indicate mutually the same position in the distance direction.

Further, for example, similarly to the examples in FIGS. 12 and 13, the display controlling function 125*c* displays the FFR value 12*c* in the position where the marker 7*b* is displayed.

In the display configured in this manner, by referring to the various types of information such as the graph 2*a*, the CPR image 7*a*, and the color bar 6*a*, it is possible to more efficiently understand the correlation between the FFR values and the blood vessel cross-sectional areas in the different positions in the coronary artery.

TWELFTH MODIFICATION EXAMPLE

In yet another example, the display controlling function 125*c* may display the information indicating the segments of the coronary artery in addition to the supplementary information indicating the structure of the coronary artery.

Figure 15:
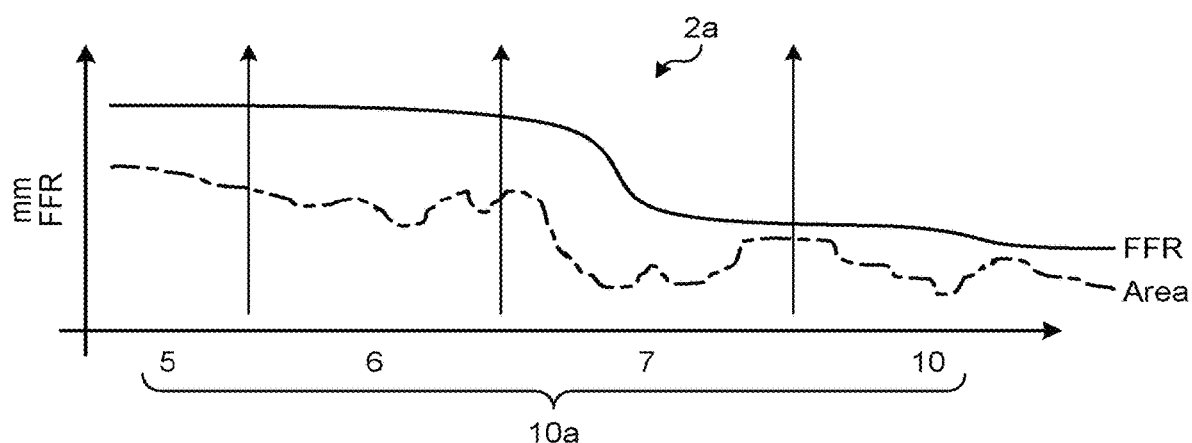
FIG. 15 is a chart illustrating an example of information displayed by a display controlling function according to a twelfth modification example.

FIG. 15 is a chart illustrating an example of information displayed by the display controlling function 125*c* according to a twelfth modification example.

For instance, as illustrated in FIG. 15, the display controlling function 125*c* may display, similarly to the example in FIG. 2, the graph 2*a* indicating the changes in FFR and in the blood vessel cross-sectional area and may also display, similarly to the examples in FIGS. 10 and 11, the numerals 10*a* indicating the segments of the coronary artery on the horizontal axis of the graph 2*a*.

In the display configured in this manner, by referring to both the information indicating the changes in the blood vessel cross-sectional area and the information indicating the segments of the coronary artery, it is possible to understand more easily and in detail the correlation between the FFR values and the blood vessel cross-sectional area in the different positions in the coronary artery.

THIRTEENTH MODIFICATION EXAMPLE

In yet another example, the display controlling function 125*c* may set a range in the distance direction along the coronary artery on the basis of anatomical information and may further display a value of the blood flow parameter obtained from a statistic value in the range, together with the graph.

Figure 16:
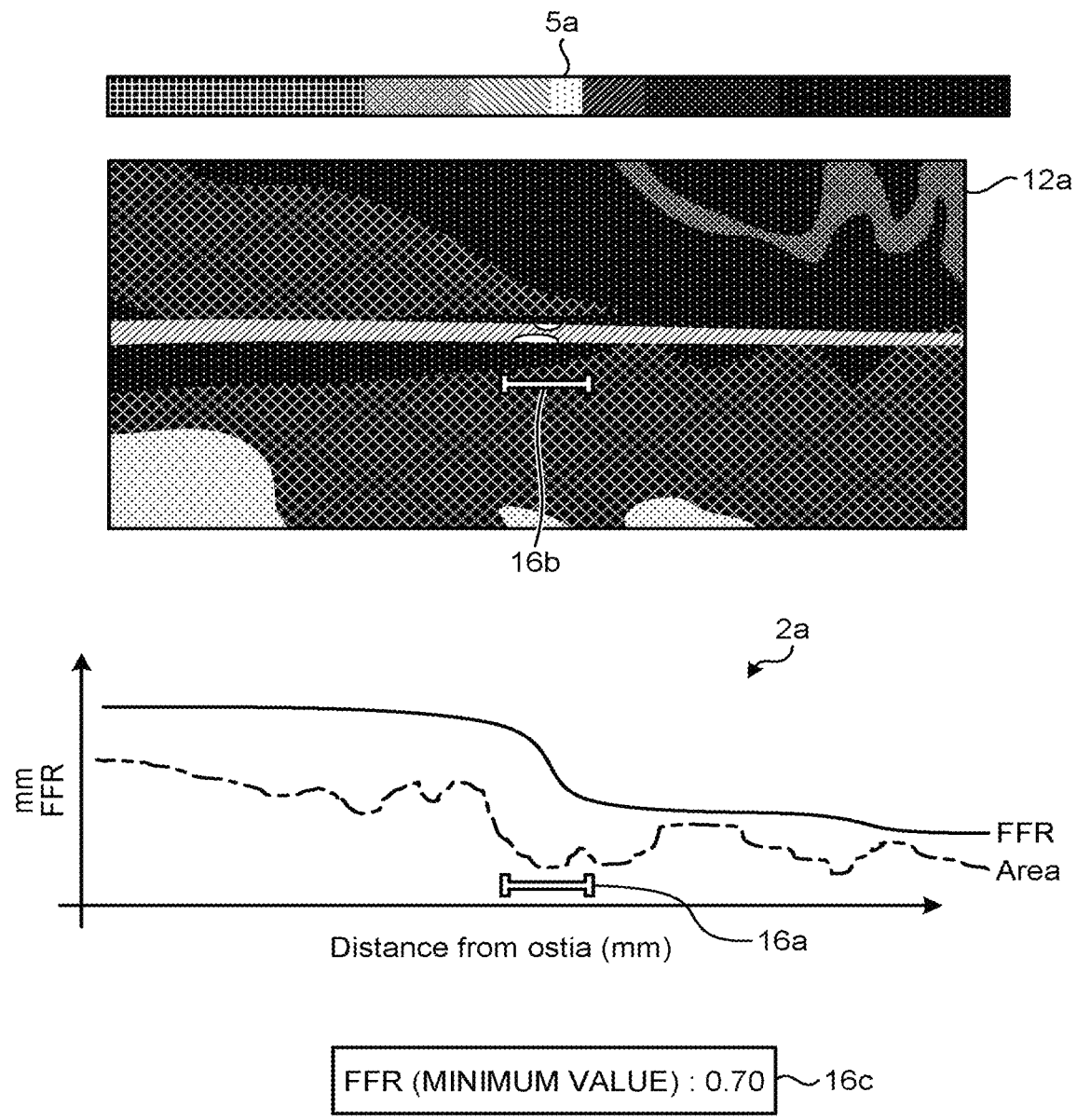
FIG. 16 is a chart illustrating an example of information displayed by a display controlling function according to a thirteenth modification example.

FIG. 16 is a chart illustrating an example of information displayed by the display controlling function 125*c* according to a thirteenth modification example.

For instance, as illustrated in FIG. 16, the display controlling function 125*c* displays the graph 2*a* indicating the changes in FFR and in the blood vessel cross-sectional area illustrated in FIG. 2 so as to be arranged alongside the CPR image 12*a* and the color par 5*a* illustrated in FIG. 12, so that the positions thereof in the distance direction are aligned with one another.

Further, in the graph 2*a* indicating the changes in FFR and in the blood vessel cross-sectional area, the display controlling function 125*c* displays a marker 16*a* indicating the range in the distance direction along the coronary artery. In addition, at the same time, the display controlling function 125*c* also displays, within the CPR image 12*a*, a similar marker 16*b* in such a position that corresponds to the position of the marker 16*b* displayed in the graph 2*a*. In the present example, the length of each of the markers 16*a* and 16*b* in the horizontal direction expresses the range in the distance direction along the coronary artery. Possible forms of the markers in the present modification example are not limited to those of the markers 16*a* and 16*b* illustrated in FIG. 16. As long as it is possible to express the range in the distance direction, it is acceptable to use markers in any shape.

Subsequently, the display controlling function 125*c* receives, from the operator, an operation to arrange the marker 16*a* in an arbitrary position within the graph 2*a*, on the basis of anatomical information indicated by the graph 2*a* or the CPR image 12*a*. In this situation, in accordance with the operation received from the operator, the display controlling function 125*c* displays the marker 16*a* in a corresponding position in the graph 2*a*. Alternatively, the display controlling function 125*c* may receive, from the operator, an operation to arrange the marker 16*b* in an arbitrary position within the CPR image 12*a*. Further, the display controlling function 125*c* receives, from the operator, a designation of a range in the distance direction, by changing the length of the marker 16*a* or 16*b* in accordance with the operation of the operator. After that, on the basis of the position and the length of the marker 16*a* or 16*b* arranged by the operator, the display controlling function 125*c* sets the range in the distance direction along the coronary artery.

Subsequently, the display controlling function 125*c* displays an FFR value obtained from a statistic value of coronary artery pressure in the set range. For example, the display controlling function 125*c* may derive the FFR value by using a minimum coronary artery pressure value in the set range and display a derived FFR value 16*c*. Alternatively, the display controlling function 125*c* may derive an FFR value by using another statistic value of the coronary artery pressure such as a maximum value, an average value, a median, a delta value, or the like. In another example, the display controlling function 125*c* may display FFR values in the set range, in the form of a numerical range such as "0.81-0.85".

Further, for example, the display controlling function 125*c* may also display a similar marker in the vicinity of a starting part of the coronary artery in the graph 2*a* and in the CPR image 12*a* so as to further receive an operation performed on the marker from the operator. In that situation, for example, the display controlling function 125*c* derives an FFR value by using a statistic value of coronary artery pressure in the range of the marker arranged in the vicinity of the starting part of the coronary artery and a statistic value of coronary artery pressure in the ranges of the markers 16*a* and 16*b* arranged in the arbitrary positions described above.

In yet another example, the display controlling function 125*c* may further display the information indicating the segments of the coronary artery, similarly to the examples in FIGS. 10, 11, and 15. In that situation, for example, the display controlling function 125*c* sets a range in the distance direction along the coronary artery by using the segments of the coronary artery as the anatomical information. For example, the display controlling function 125*c* may set the range in the distance direction along the coronary artery, in units of the segments of the coronary artery. In other words, in that situation, the display controlling function 125*c* sets either a section corresponding to one segment or a section corresponding to a plurality of successive segments, as the range in the distance direction along the coronary artery.

FOURTEENTH MODIFICATION EXAMPLE

In yet another example, the display controlling function 125c may further display functional information about a myocardium of the subject, together with the graph indicating the changes in values of the blood flow parameter.

In that situation, in addition to the CT image data related to the coronary artery of the subject, the obtaining function 125a further obtains volume data indicating the functional information about the myocardium of the subject.

For example, the obtaining function 125a obtains volume data of a CT perfusion image taken of the myocardium by injecting a contrast agent to the subject. Alternatively, for example, the obtaining function 125a may obtain volume data generated by another medical image diagnosis apparatus such as a Magnetic Resonance Imaging (MRI) apparatus, an ultrasound diagnosis apparatus, an X-ray diagnosis apparatus, or a Positron Emission Tomography (PET) apparatus. As for the volume data in the present modification example, it is possible to use any volume data, as long as the volume data indicates the functional information about the myocardium.

Further, on the basis of the volume data obtained by the obtaining function 125a, the display controlling function 125c displays the functional information about the myocardium of the subject, together with the graph indicating the changes in values of the blood flow parameter.

More specifically, the display controlling function 125c specifies a dominant region of the coronary artery in the myocardium and displays a myocardial index value in the dominant region as the functional information about the myocardium.

For example, the display controlling function 125c generates a polar map indicating the functional information about the myocardium by using the volume data obtained by the obtaining function 125a and displays the generated polar map together with the graph indicating the changes in values of the blood flow parameter. In the present example, the polar map is an image in which the three-dimensional shape of the myocardium is developed onto a plane and simulatively expressed with a circular figure, so that the functional information about the myocardium is mapped on the figure.

FIGS. 17A to 17D are charts illustrating an example of information displayed by the display controlling function 125c according to a fourteenth modification example.

Figure 17B:
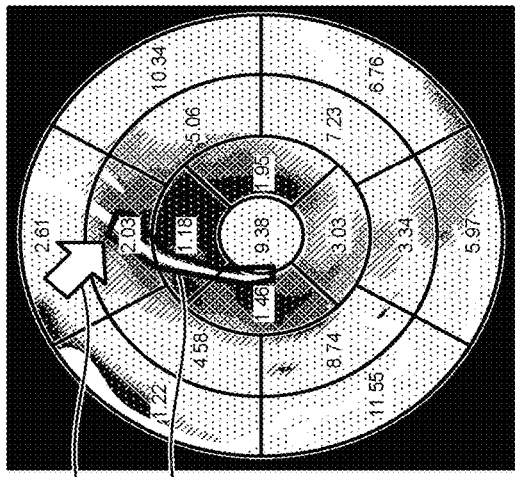
FIGS. 17A to 17D are charts illustrating an example of information displayed by a display controlling function according to a fourteenth modification example.
Figure 17D:
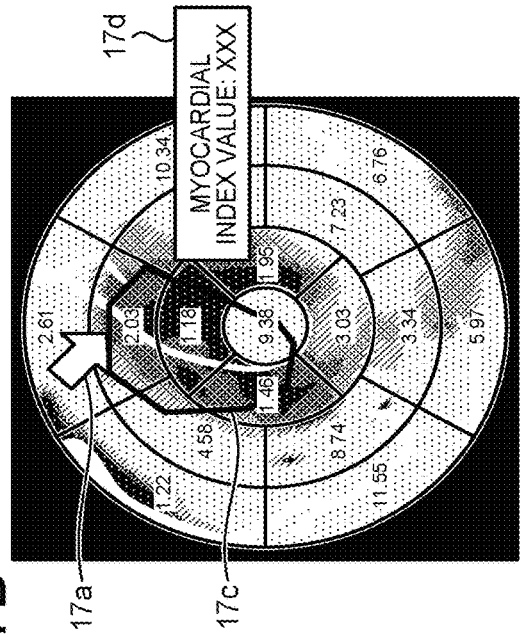
Figure 17A:
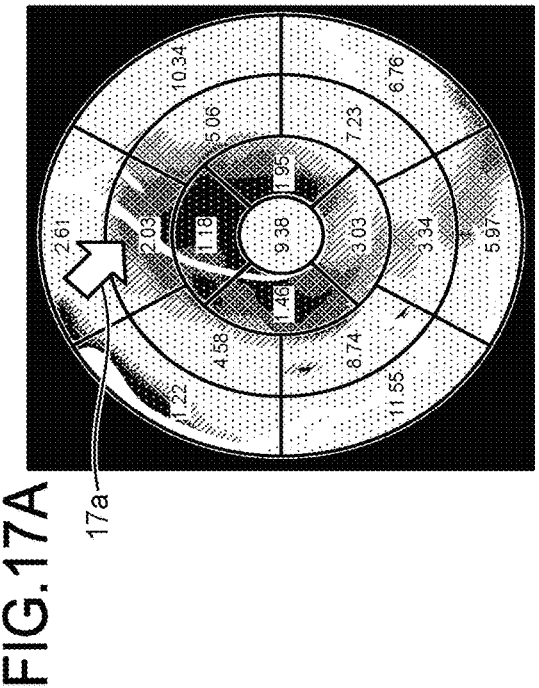

For instance, as illustrated in FIG. 17A, the display controlling function 125c generates an image in which a blood vessel image of the coronary artery is projected onto the polar map expressing the functional information about the myocardium in color and further displays the generated image together with the graph (not illustrated) indicating the changes in values of the blood flow parameter. Also, the display controlling function 125c displays a marker 17a in the polar map and receives, from the operator, an operation to arrange the marker 17a in an arbitrary position.

Figure 17C:
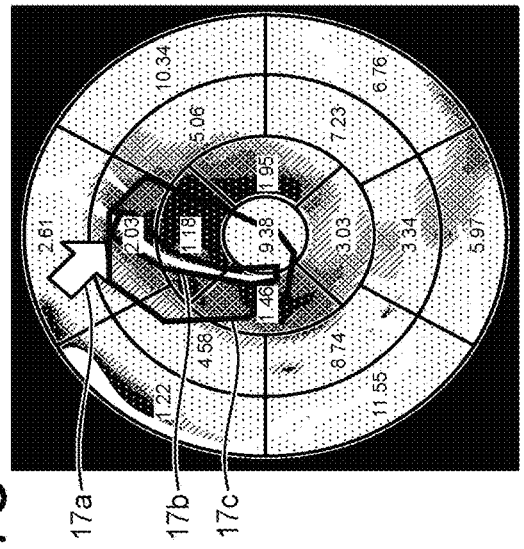

In this situation, as illustrated in FIG. 17B, when the marker 17a is arranged in the blood vessel image of the coronary artery, the display controlling function 125c specifies a blood vessel region 17b positioned on the downstream side of the position of the marker 17a. After that, as illustrated in FIG. 17C, the display controlling function 125c specifies a myocardial dominant region 17c, which is a region of the myocardium to which blood is supplied from the specified blood vessel region 17b. For example, by using a Voronoi algorithm or the like, the display controlling function 125c specifies the myocardial dominant region 17c.

After that, as illustrated in FIG. 17D, the display controlling function 125c derives a myocardial index value in the specified myocardial dominant region 17c and displays a derived myocardial index value 17d. In this situation, for example, the myocardial index value may be an integrated value obtained by integrating myocardial index values in the myocardial dominant region 17c or an average value obtained by averaging myocardial index values in the myocardial dominant region 17c.

In the description above, the example was explained in which the display controlling function 125c displays the functional information about the myocardium by using the polar map; however, the present modification example is not limited to this example. For instance, the display controlling function 125c may display the functional information about the myocardium by using a graph or by using a color bar.

FIFTEENTH MODIFICATION EXAMPLE

In yet another example, the display controlling function 125c may further derive, by a simulation, informatio indicating a change in functional information about the myocardium when the coronary artery is deformed by the treatment simulation, and display the derived information together with the graph indicating the changes in values of the blood flow parameter.

In that situation, the analyzing function 125b further derives values of the blood flow parameter expected after the coronary artery is treated, by performing the treatment simulation on the coronary artery while using the CT image data obtained by the obtaining function 125a.

After that, the display controlling function 125c further displays, by performing a simulation using the blood flow parameter after the treatment derived by the analyzing function 125b, information indicating a change in functional information about the myocardium when the coronary artery is deformed by the treatment simulation, together with the graph indicating the changes in values of the blood flow parameter.

For example, the display controlling function 125c derives functional information about the myocardial before the treatment by performing a simulation using the blood flow parameter before the treatment which is derived before the treatment simulation is performed. Further, the display controlling function 125c derives functional information about the myocardial after the treatment by performing a simulation using the blood flow parameter after the treatment. Further, the display controlling function 125c displays the functional information about the myocardial before the treatment and the information about the myocardial after the treatment as the information indicating the change in functional information about the myocardium.

In this situation, for example, the display controlling function 125c may specify a dominant region of the coronary artery in the myocardium, derive a myocardial index value before the treatment in the dominant region as the functional information about the myocardium before the treatment, and derive a myocardial index value after the treatment in the dominant region as the functional information about the myocardium after the treatment.

For example, the analyzing function 125b derives values of the blood flow parameter before a treatment of the coronary artery, by performing a fluid analysis while using the CT image data obtained by the obtaining function 125a, similarly to the first embodiment.

After that, for example, the display controlling function 125c specifies a dominant region of the coronary artery in the myocardium, and then derives a flow amount of blood supplied to the dominant region based on the blood flow parameter before the treatment derived by the analyzing function 125b. Further, the display controlling function 125c generates a myocardium perfusion image before the treatment by performing a simulation that simulatively derives spatial distribution of perfusion values of the myocardium while using the derived flow amount of blood. In this situation, the perfusion value is an example of the myocardial index value.

After that, the analyzing function 125b performs a treatment simulation that virtually performs a treatment for the coronary artery while using the CT image data obtained by the obtaining function 125a. In this situation, as a method for the treatment simulation, it is possible to use any of various types of publicly-known methods.

Further, the analyzing function 125b derives values of the blood flow parameter after the treatment of the coronary artery, by performing a fluid analysis again while using data of the coronary artery virtually deformed by the treatment simulation.

After that, the display controlling function 125c derives a flow amount of blood supplied to the dominant region based on the blood flow parameter after the treatment derived by the analyzing function 125b, and generates a myocardium perfusion image after the treatment by performing a simulation using the derived flow amount of blood.

Then, the display controlling function 125c displays, as the information indicating the change in functional information about the myocardium, the myocardium perfusion image before the treatment generated before the treatment simulation is performed, and the myocardium perfusion image after the treatment generated after the treatment simulation is performed, side by side.

In the display configured in this manner, the operator can easily see the amount of myocardium (dominant region) impacted by the treatment.

Further, in the above modification example, images to indicate the spatial distribution of perfusion values of the myocardium are not limited to the myocardium perfusion image. For example, the spatial distribution of perfusion values of the myocardium may be indicated by a form of a polar map, or may be displayed by displaying a volume rendering image of the myocardium and the coronary artery, and adding colors according to the perfusion values to a part of the myocardium in the volume rendering image. By using the volume rendering image, the operator can understand the correlation between the coronary artery, FFR and the perfusion value even better.

SIXTEENTH MODIFICATION EXAMPLE

In yet another example, the display controlling function 125c may further display, by using a graph, information indicating changes in values of the blood flow parameter expected after treatment that is obtained by performing a treatment simulation.

In that situation, the analyzing function 125b further derives values of the blood flow parameter expected after the coronary artery is treated, by performing the treatment simulation on the coronary artery while using the CT image data obtained by the obtaining function 125a. Also, by performing the treatment simulation, the analyzing function 125b may further derive values of the morphological parameter expected after the coronary artery is treated.

After that, the display controlling function 125c further displays information indicating changes in values of the blood flow parameter expected after the treatment that is derived by the analyzing function 125b, in the graph indicating the changes in values of the blood flow parameter. Also, the display controlling function 125c may further display information indicating changes in values of the morphological parameter expected after the treatment that is derived by the analyzing function 125b, in the graph indicating the changes in values of the blood flow parameter.

For example, the analyzing function 125b may perform a treatment simulation for inserting a treatment device in the coronary artery. In the following sections, an example will be explained in which the analyzing function 125b performs a treatment simulation for inserting a stent in the coronary artery.

Figure 19:
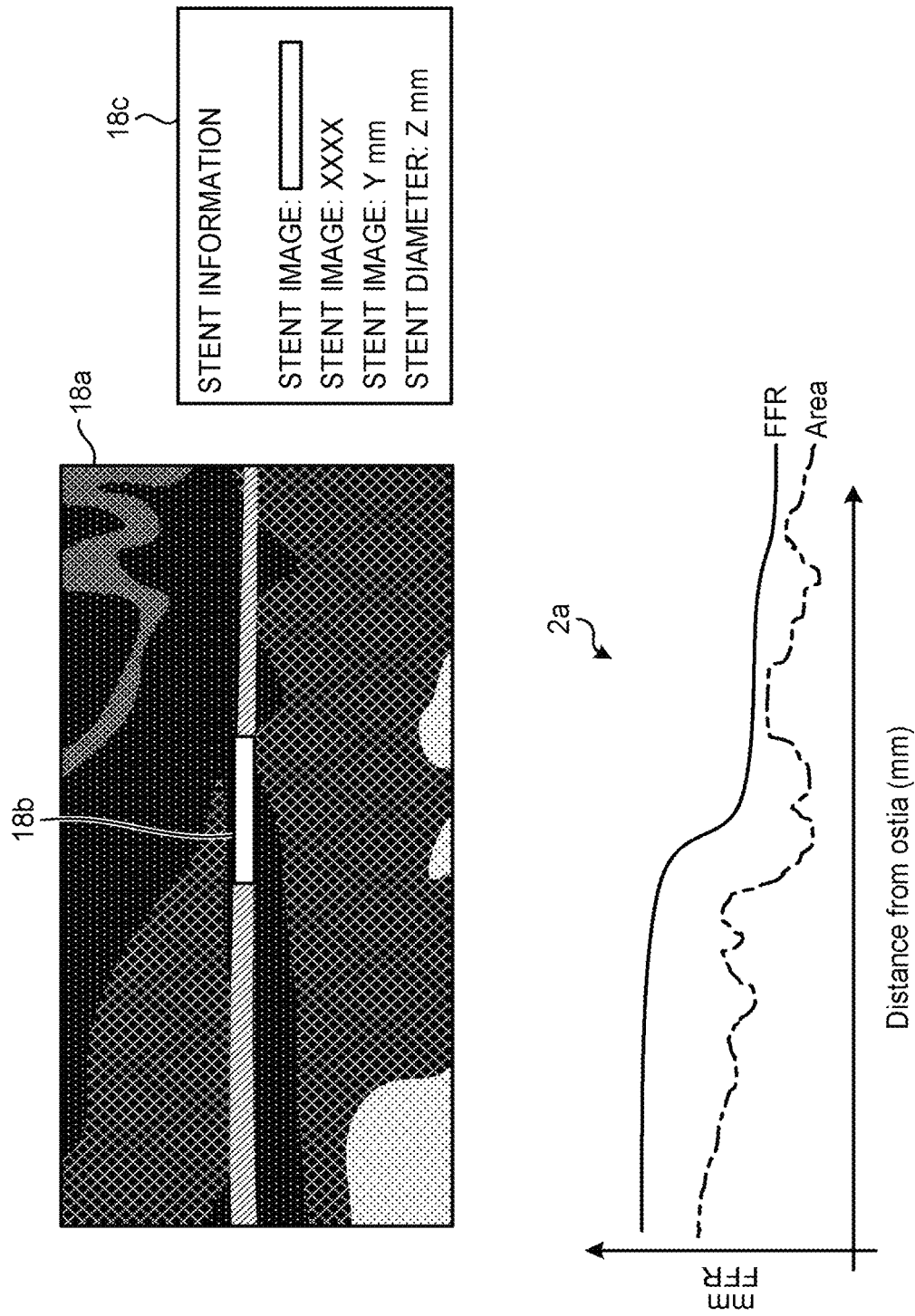
FIG. 19 is a chart illustrating another example of the information displayed by the display controlling function according to the sixteenth modification example.
Figure 20:
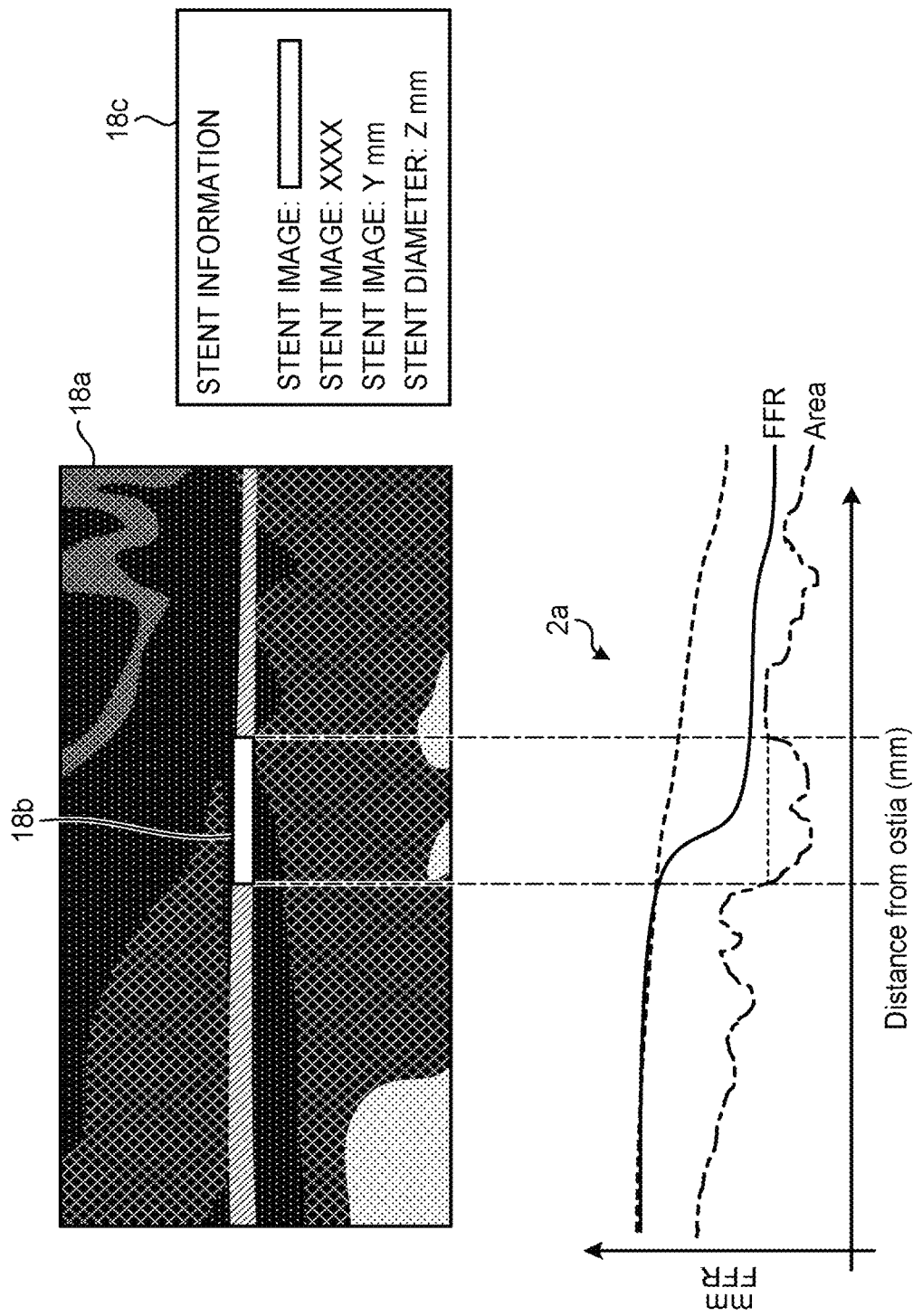
FIG. 20 is a chart illustrating yet another example of the information displayed by the display controlling function according to the sixteenth modification example.

FIGS. 18 to 20 are charts illustrating examples of information displayed by the display controlling function 125c according to a sixteenth modification example.

For instance, as illustrated in FIG. 18, the display controlling function 125c displays the graph 2a indicating the changes in FFR and in the blood vessel cross-sectional area illustrated in FIG. 2, alongside a Stretched Curved Planar Reconstruction (SPR) image 18a of the coronary artery generated on the basis of the CT image data, so that the positions thereof in the distance direction are aligned with each other.

Further, for example, as illustrated in FIG. 19, the display controlling function 125c displays a stent image 18b simulatively indicating the shape of the treatment stent within the SPR image 18a and further receives an operation from the operator to arrange the stent image 18b in an arbitrary position in the coronary artery. In this situation, for example, the display controlling function 125c receives, from the operator, designations of a length, a diameter, and an insertion position of the stent, by changing the shape of the stent image 18b in accordance with the operation of the operator. In this situation, for example, the display controlling function 125c displays stent information 18c indicating a stent image, a stent model number, the stent length, and the stent diameter, together with the graph 2a and the SPR image 18a.

After that, the analyzing function 125b performs the treatment simulation, by performing a fluid analysis again while applying the length, the thickness, and the insertion position of the stent designated by the operator with the use of the stent image 18b, to the analysis model generated from the CT image at the time of the initial fluid analysis. Accordingly, for example, the analyzing function 125b is configured to derive the FFR value and the blood vessel cross-sectional area expected after the treatment.

Further, for example, as illustrated in FIG. 20, the display controlling function 125c displays curves (the curves of dotted lines in FIG. 20) indicating the changes in FFR and in the blood vessel cross-sectional area expected after the treatment that were derived by the analyzing function 125b, so as to be superimposed on the curves indicating the changes in FFR and in the blood vessel cross-sectional area before the treatment in the graph 2a. In this situation, for example, the display controlling function 125c further displays information (the straight dashed lines in FIG. 20) indicating a starting point and an ending point of the stent, in the graph 2a.

In the display configured in this manner, it is possible to easily understand how much the FFR value and the blood vessel cross-sectional area will change when the treatment is performed, by comparing the information prior to the treatment with the information after the treatment.

With reference to FIG. 20, the example was explained in which the display controlling function 125c displays the curves indicating the changes in FFR and in the blood vessel cross-sectional area expected after the treatment so as to be superimposed on the curves indicating the changes in FFR and in the blood vessel cross-sectional area before the treatment; however, the present modification example is not limited to this example. For instance, the display controlling function 125c may display the curves indicating the changes expected after the treatment, so as to be arranged next to the curves indicating the changes prior to the treatment. Alternatively, in accordance with operations from the operator, the display controlling function 125c may switch the display between the curves indicating the changes expected after the treatment and the curves indicating the changes prior to the treatment.

Further, in the above description, the example was explained in which the analyzing function 125b performs the treatment simulation for inserting the stent in the coronary artery; however, the present modification example is not limited to this example. For instance, the analyzing function 125b may perform a treatment simulation for expanding the inside diameter of the blood vessel by scraping a stenosis site in the coronary artery. In yet another example, the analyzing function 125b may perform a treatment simulation for inserting a balloon in the coronary artery and dilating the inner wall of the coronary artery by the balloon. In yet another example, the analyzing function 125b may perform a treatment simulation for changing a blood flow parameter (e.g., viscosity) by administering a drug for the subject.

Further, in the above description, the example was explained in which the display controlling function 125c displays only the results (the SPR image, the FFR values, and the blood vessel cross-sectional areas) of the treatment simulation for inserting the stent in the coronary artery; however, the present modification example is not limited to this example. For instance, the display controlling function 125c may display results of a plurality of types of treatment simulations performed by the analyzing function 125b. In an example, the display controlling function 125c may display: a result of having a blood vessel diameter of 3 mm and a blood vessel length of 5 mm; a result of having a blood vessel diameter of 3 mm and a blood vessel length of 7 mm; and a result of changing the blood flow parameter with the administration of the drug. In that situation, the display controlling function 125c may display the results so as to be superimposed on one another, may display the results arranged next to one another, or may switch between the displays in accordance with operations of the operator.

OTHER MODIFICATION EXAMPLES

In the first embodiment and the modification examples above, when displaying the CPR image of the coronary artery like in the examples of FIGS. 7, 8, and 12 to 14, the display controlling function 125c may display, for example, a linear graphic element indicating the outline of the coronary artery so as to be superimposed on the CPR image.

In that situation, for example, the display controlling function 125c may switch between a mode where the graphic element is displayed and another mode where the graphic element is not displayed, in accordance with instructions from the operator. For example, when the graphic element is displayed, the graphic element may make it difficult to observe the blood vessel within the CPR image in some situations. Accordingly, with the configuration where it is possible to switch between the display modes, the operator becomes able to easily observe the blood vessel in accordance with the situations.

Second Embodiment

In the first embodiment above, the example was explained in which the processing circuitry 125 of the medical image processing apparatus 120 includes the obtaining function 125a, the analyzing function 125b, and the display controlling function 125c; however, these processing functions may be installed in a plurality of apparatuses in a distributed manner. Thus, in the following sections, an example will be explained as a second embodiment in which the processing functions of the processing circuitry 125 described in the first embodiment are installed in two apparatuses in a distributed manner.

Figure 21:
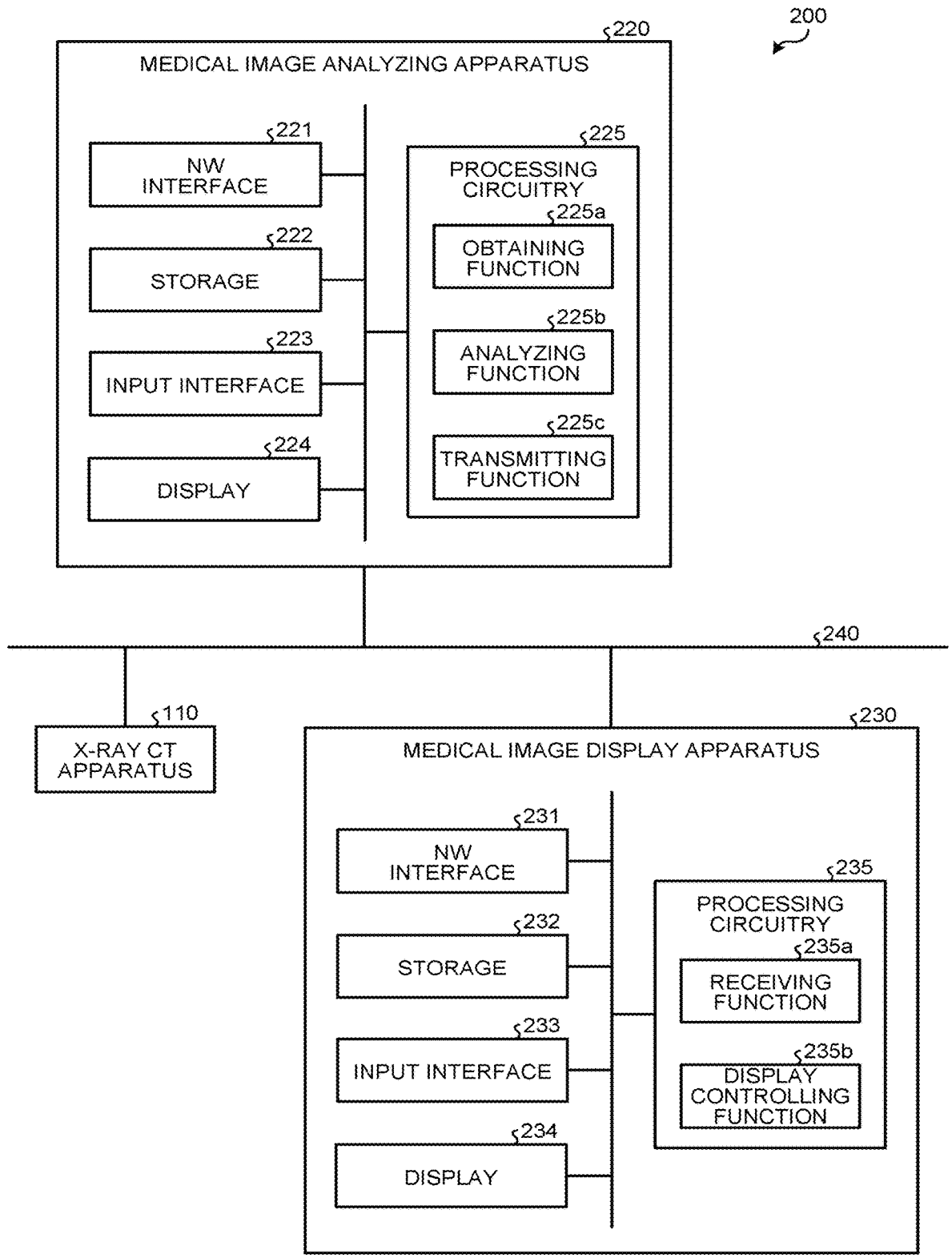
FIG. 21 is a diagram illustrating an exemplary configuration of a medical image processing system according to a second embodiment.

FIG. 21 is a diagram illustrating an exemplary configuration of a medical image processing system according to the second embodiment.

For example, as illustrated in FIG. 21, a medical image processing system 200 according to the present embodiment includes the X-ray CT apparatus 110, a medical image analyzing apparatus 220, and a medical image display apparatus 230. In the present example, the apparatuses are communicably connected to one another via a network 240.

Similarly to the first embodiment, the X-ray CT apparatus 110 is configured to generate the CT image data related to the subject.

The medical image analyzing apparatus 220 is configured to obtain the CT image data from the X-ray CT apparatus 110 via the network 240 and to perform various types of analyzing processes on the basis of the obtained CT image data. For example, the medical image analyzing apparatus 220 is realized by using a computer device such as a server, a workstation, a personal computer, or the like.

More specifically, the medical image analyzing apparatus 220 includes a NW interface 221, storage 222, an input interface 223, a display 224, and processing circuitry 225. In this situation, the NW interface 221, the storage 222, the input interface 223, and the display 224 have the same configurations as the NW interface 121, the storage 122, the input interface 123, and the display 124 of the medical image processing apparatus 120 described in the first embodiment, respectively.

The medical image display apparatus 230 is configured to obtain the CT image data from the X-ray CT apparatus 110 via the network 240 and to perform various types of analyzing processes on the basis of the obtained CT image data. For example, the medical image display apparatus 230 is realized by using a computer device such as a server, a workstation, a personal computer, or the like.

More specifically, the medical image display apparatus 230 includes a NW interface 231, storage 232, an input interface 233, a display 234, and processing circuitry 235. In the present example, the NW interface 231, the storage 232, the input interface 233, and the display 234 have the same configurations as the NW interface 121, the storage 122, the input interface 123, and the display 124 of the medical image processing apparatus 120 described in the first embodiment, respectively.

Further, in the present embodiment, the processing circuitry 225 of the medical image analyzing apparatus 220 includes an obtaining function 225a, an analyzing function 225b, and a transmitting function 225c. The obtaining function 225a is an example of the obtaining unit. The analyzing function 225b is an example of the analyzing unit.

The obtaining function 225a is configured to perform the same processes as those performed by the obtaining function 125a described in the first embodiment or the modification examples. The analyzing function 225b is configured to perform the same processes as those performed by the analyzing function 125b described in the first embodiment or the modification examples. The transmitting function 225c is configured to transmit information including the values of the blood flow parameter and the morphological parameter derived by the analyzing function 225b, to the medical image display apparatus 230 via the NW interface 221.

Further, in the present embodiment, the processing circuitry 235 of the medical image display apparatus 230 includes a receiving function 235a and a display controlling function 235b. The display controlling function 235b is an example of the display controlling unit.

The receiving function 235a is configured to receive, via the NW interface 231, the information including the values of the blood flow parameter and the morphological parameter transmitted thereto from the medical image analyzing apparatus 220. Further, by using the information received by the receiving function 235a, the display controlling function 235b is configured to perform the same processes as those performed by the display controlling function 125c described in the first embodiment or the modification examples.

With these arrangements, for example, the display controlling function 235b is configured to display the information indicating the changes in values of the blood flow parameter along the coronary artery, by using the graph of which the vertical axis expresses the values of the blood flow parameter and of which the horizontal axis corresponds to the distance direction along the coronary artery and is configured to further display the supplementary information indicating the structure of the coronary artery together with the graph.

Alternatively, for example, the display controlling function 235b may be configured to display the information indicating the changes in values of the blood flow parameter along the coronary artery by using the graph of which the vertical axis expresses the values of the blood flow parameter and of which the horizontal axis corresponds to the distance direction along the coronary artery and may be configured to further display the information indicating the segments of the coronary artery on the horizontal axis of the graph.

In the present embodiment, for example, the analyzing function 225b of the medical image analyzing apparatus 220 is configured, similarly to the first embodiment or the modification examples, to generate the display-purpose data for displaying the information on the basis of the derived values of the blood flow parameter and the morphological parameter and to transmit the generated display-purpose data to the medical image display apparatus 230, so that the display controlling function 235b of the medical image display apparatus 230 displays the information on the basis of the received display-purpose data. Alternatively, for example, the analyzing function 225b of the medical image analyzing apparatus 220 may be configured to transmit the values of the blood flow parameter and the morphological parameter to the medical image display apparatus 230, so that the display controlling function 235b of the medical image display apparatus 230 displays the information by using the received values of the blood flow parameter and the morphological parameter, similarly to the display controlling function 125c described in the first embodiment or the modification examples.

In these situations, for example, the processing circuitry 225 of the medical image analyzing apparatus 220 and the processing circuitry 235 of the medical image display apparatus 230 are each realized by using a processor. In that situation, each of the processing functions of the pieces of processing circuitry is stored in storage of the corresponding apparatus in the form of a computer-executable program. Further, each of the pieces of processing circuitry is configured to realize the processing functions corresponding to the programs by reading and executing the programs from the storage. In other words, when having read the programs, each of the pieces of processing circuitry has the processing functions illustrated in FIG. 21.

With the configurations described above, in the second embodiment also, it is possible, similarly to the first embodiment, to easily understand the correspondence relationship between the positions from which the values of the blood flow parameter were derived and the positions in the coronary artery, by referring to the supplementary information together with the graph.

Third Embodiment

Further, the processing functions of the processing circuitry 125 described in the first embodiment may be installed in an X-ray CT apparatus. Thus, in the following sections, an example will be explained as a third embodiment in which the processing functions of the processing circuitry 125 described in the first embodiment are installed in an X-ray CT apparatus.

Figure 22:
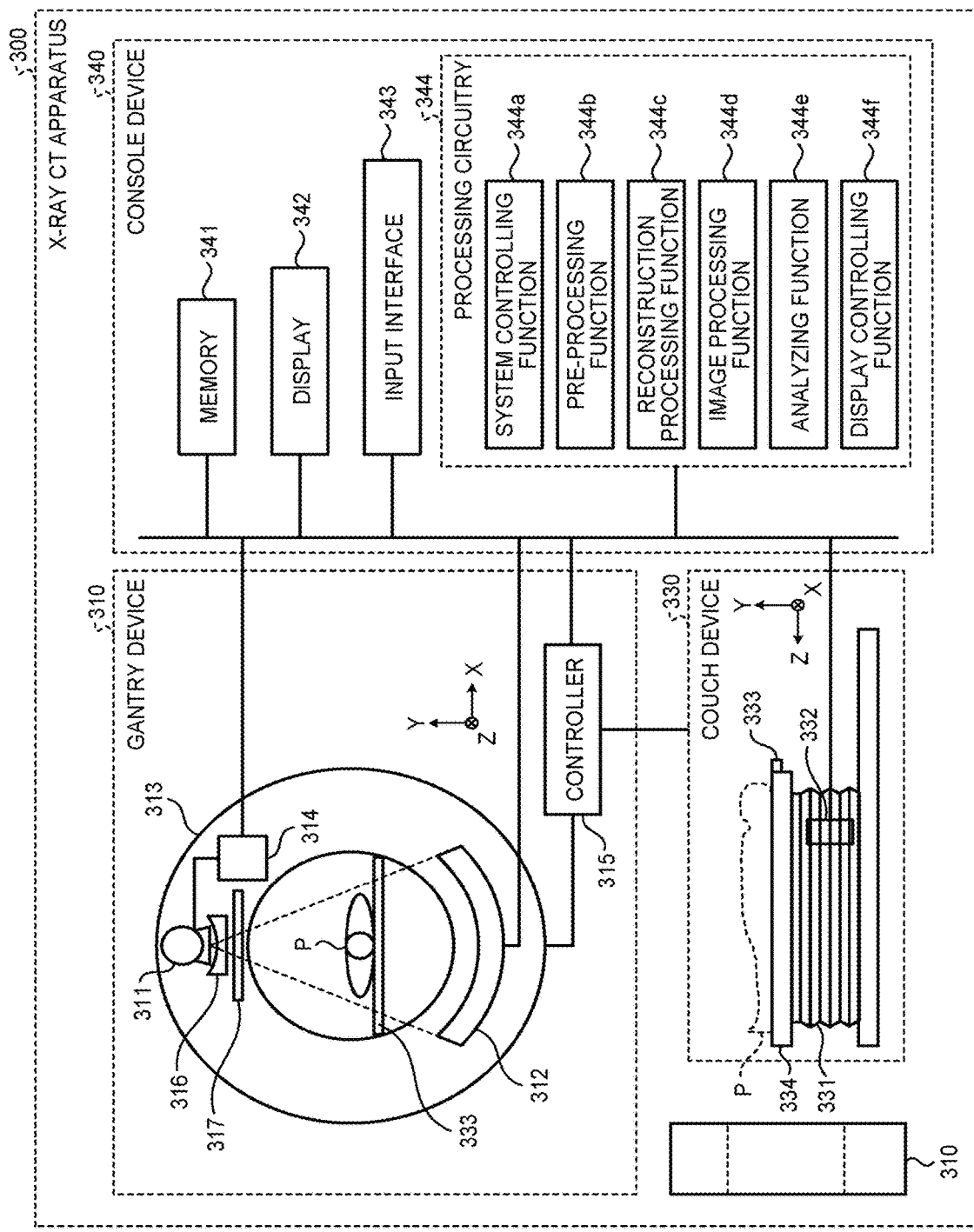
FIG. 22 is a diagram illustrating an exemplary configuration of an X-ray CT apparatus according to a third embodiment.

FIG. 22 is a diagram illustrating an exemplary configuration of the X-ray CT apparatus according to the third embodiment.

For example, as illustrated in FIG. 22, an X-ray CT apparatus 300 according to the present embodiment includes a gantry device 310, a couch device 330, and a console device 340. For the sake of convenience in the explanation, FIG. 22 illustrates the gantry device 310 in multiple locations.

In the present embodiment, the rotation axis of a rotating frame 313 in a non-tilted state or the longitudinal direction of a couchtop 333 of the couch device 330 is defined as a "Z-axis direction". Further, the axial direction orthogonal to the Z-axis direction and parallel to the floor surface is defined as an "X-axis direction". The axial direction orthogonal to the Z-axis direction and perpendicular to the floor surface is defined as a "Y-axis direction".

The gantry device 310 is a device configured to radiate X-rays onto a subject (for example, a patient) P, to detect X-rays that have passed through the subject P, and to output a detection result to the console device 340. The gantry device 310 includes an X-ray tube 311, an X-ray detector 312, a rotating frame 313, an X-ray high-voltage device 314, a controller 315, a wedge 316, and an X-ray limiter 317.

The X-ray tube 311 is a vacuum tube configured to generate the X-rays by emitting thermo electrons from a negative pole (a filament) toward a positive pole (a target), with high voltage applied by the X-ray high-voltage device 314. For example, the X-ray tube 311 is a rotating anode X-ray tube configured to generate the X-rays by emitting the thermo electrons onto a rotating anode (positive pole).

The wedge 316 is a filter used for adjusting the X-ray dose of the X-rays radiated from the X-ray tube 311. More specifically, the wedge 316 is a filter configured to pass and attenuate the X-rays radiated from the X-ray tube 311, so that the X-rays radiated from the X-ray tube 311 onto the subject P have a predetermined distribution. For example, the wedge 316 is a filter obtained by processing aluminum so as to have a predetermined target angle and a predetermined thickness. The wedge 316 may be referred to as a wedge filter or a bow-tie filter.

The X-ray limiter 317 includes lead plates or the like used for narrowing down the radiation range of the X-rays that have passed through the wedge 316 and is configured to form a slit with a combination of the plurality of lead plates or the like.

The X-ray detector 312 is configured to detect the X-rays that were radiated from the X-ray tube 311 and have passed through the subject P. More specifically, the X-ray detector 312 includes a plurality of rows of detecting elements in each of which a plurality of detecting elements are arranged in a channel direction along an arc centered on a focal point of the X-ray tube 311. For example, the X-ray detector 312 has a structure in which the plurality of rows of detecting elements are arranged in a row direction (which may be called a slice direction), the plurality of rows each having the plurality of detecting elements arranged in the channel direction.

For example, the X-ray detector 312 is a detector of an indirect conversion type including a collimator, a scintillator array, and an optical sensor array. The scintillator array includes a plurality of scintillators. Each of the scintillators includes a scintillator crystal that outputs light having a photon quantity corresponding to the amount of the X-rays that have become incident thereto. The collimator (which may also be called a grid) is disposed on the surface of the scintillator array positioned on the X-ray incident side and includes an X-ray blocking plate that absorbs scattered X-rays. For example, the collimator may be a one-dimensional collimator or a two-dimensional collimator. The optical sensor array includes a plurality of optical sensors. Each of the optical sensors is configured to output an electrical signal corresponding to the quantity of light output from a corresponding one of the scintillators. For example, the optical sensor array includes other optical sensors such as photomultiplier tubes (PMTs). Alternatively, the X-ray detector 312 may be a detector of a direct conversion type including a semiconductor element configured to convert the incident X-rays into electrical signals.

Further, the X-ray detector 312 includes a Data Acquisition System (DAS) configured to process the electrical signals output from the detecting elements. The DAS includes an amplifier configured to perform an amplifying process on the electrical signals output from the detecting elements of the X-ray detector 312; and an Analog/Digital (A/D) converter configured to convert the electrical signals into digital signals. The DAS is configured to generate detection data. The detection data generated by the DAS is transferred to the console device 340.

The X-ray high-voltage device 314 includes: a high-voltage generating device including electrical circuits such as a transformer, a rectifier, and the like and having a function of generating the high voltage to be applied to the X-ray tube 311; and an X-ray controller configured to control the output voltage in accordance with the X-ray output radiated by the X-ray tube 311. The high-voltage generating device may be of a transformer type or of an inverter type. Further, the X-ray high-voltage device 314 may be provided on the rotating frame 313 or may be provided on a supporting frame (not illustrated) configured to rotatably support the rotating frame 313 in the gantry device 310.

The rotating frame 313 is an annular frame configured to support the X-ray tube 311 and the X-ray detector 312 so as to oppose each other and configured to rotate the X-ray tube 311 and the X-ray detector 312 via the controller 315 (explained later). In addition to supporting the X-ray tube 311 and the X-ray detector 312, the rotating frame 313 further includes and supports the X-ray high-voltage device 314. In an example, the detection data generated by the DAS included in the X-ray detector 312 is transmitted from a transmitter including a Light Emitting Diode (LED) and being provided on the rotating frame 313, to a receiver including a photodiode and being provided in a non-rotation part (e.g., the supporting frame) of the gantry device 310, through optical communication, and is further transferred to the console device 340. The method for transmitting the detection data from the rotating frame 313 to the non-rotation part of the gantry device 310 is not limited to the optical communication described above and may be realized with any of other contactless data transfer methods.

The controller 315 includes: processing circuitry having a Central Processing Unit (CPU) or the like; and a driving mechanism configured with a motor, an actuator, and/or the like. Upon receipt of an input signal from an input interface 343 attached to the console device 340 or to the gantry device 310, the controller 315 has a function of controlling operations of the gantry device 310 and the couch device 330. Further, upon receipt of input signals, the controller 315 is configured to exercise control so as to rotate the rotating frame 313, to tilt the gantry device 310, and to bring the couch device 330 and the couchtop 333 into operation. For example, the control to tilt the gantry device 310 is realized as a result of the controller 315 rotating the rotating frame 313 on an axis parallel to the X-axis direction, on the basis of tilting angle (tilt angle) information input through the input interface 343 attached to the gantry device 310. The controller 315 may be provided for the gantry device 310 or for the console device 340.

The couch device 330 is a device on which the subject P to be scanned is placed and which is configured to move the subject P. The couch device 330 includes a base 331, a couch driving device 332, the couchtop 333, and a supporting frame 334. The base 331 is a casing configured to support the supporting frame 334 so as to be movable in the vertical directions. The couch driving device 332 is a motor or an actuator configured to move the couchtop 333 on which the subject P is placed, along the long axis directions thereof. The couchtop 333 provided on the top face of the supporting frame 334 is a board on which the subject P is placed. In addition to the couchtop 333, the couch driving device 332 may also move the supporting frame 334 along the long axis directions of the couchtop 333.

The console device 340 is a device configured to receive operations performed by an operator on the X-ray CT apparatus 300 and to also reconstruct CT image data by using the detection data acquired by the gantry device 310. The console device 340 includes a memory 341, a display 342, the input interface 343, and processing circuitry 344. In the present example, the console device 340 and the gantry device 310 are separate from each other; however, another arrangement is also acceptable in which the gantry device 310 includes the console device 340 or one or more of the constituent elements of the console device 340.

The memory 341 is realized by using, for example, a semiconductor memory element such as a Random Access Memory (RAM) or a flash memory, or a hard disk, an optical disk, or the like. For example, the memory 341 is configured to store therein the projection data and the CT image data.

The display 342 is configured to display various types of information. For example, the display 342 is configured to output medical images (CT images) generated by the processing circuitry 344, a Graphical User Interface (GUI) used for receiving various types of operations from the operator, and the like. For example, the display 342 is a liquid crystal display or a Cathode Ray Tube (CRT) display. Alternatively, the display 342 may be provided for the gantry device 310, for example. Further, for example, the display 342 may be of a desktop type or may be configured by using a tablet terminal or the like capable of wirelessly communicating with the main body of the console device 340.

The input interface 343 is configured to receive various types of input operations from the operator, to convert the received input operations into electrical signals, and to output the electrical signals to the processing circuitry 344. For example, the input interface 343 is configured to receive, from the operator, an acquisition condition used at the time of acquiring the projection data, a reconstruction condition used at the time of reconstructing the CT image data, an image processing condition used at the time of generating a post-processing image from a CT image, and the like. For example, the input interface 343 is realized by using a mouse, a keyboard, a trackball, a switch, a button, a joystick, and/or the like. Alternatively, for example, the input interface 343 may be provided for the gantry device 310. Further, for example, the input interface 343 may be configured by using a tablet terminal or the like capable of wirelessly communicating with the main body of the console device 340.

The processing circuitry 344 is configured to control operations of the entirety of the X-ray CT apparatus 300. For example, the processing circuitry 344 includes a system controlling function 344a, a pre-processing function 344b, a reconstruction processing function 344c, and an image processing function 344d.

The system controlling function 344a is configured to control various types of functions of the processing circuitry 344, on the basis of the input operations received from the operator via the input interface 343. For example, the system controlling function 344a is configured to control a CT scan performed by the X-ray CT apparatus 300. Further, the system controlling function 344a is configured to control the generation and the display of the CT image data by the console device 340, by controlling the pre-processing function 344b, the reconstruction processing function 344c, and the image processing function 344d.

The pre-processing function 344b is configured to generate the projection data obtained by performing pre-processing processes such as a logarithmic conversion process, an offset correcting process, an inter-channel sensitivity correcting process, a beam hardening correction, and/or the like on the detection data output from the DAS included in the X-ray detector 312. The data (the detection data) before the pre-processing processes and the data after the pre-processing processes may collectively be referred to as the projection data.

The reconstruction processing function 344c is configured to generate the CT image data (reconstructed image data) by performing a reconstructing process using a filtered back projection method, a successive approximation reconstruction method, or the like, on the projection data generated by the pre-processing function 344b.

On the basis of an input operation received from the operator via the input interface 343, the image processing function 344d is configured to convert the CT image data generated by the reconstruction processing function 344c into tomographic image data or three-dimensional image data on an arbitrary cross-sectional plane, by using a publicly-known method. Alternatively, the three-dimensional image data may directly be generated by the reconstruction processing function 344c.

Further, in the present embodiment, the system controlling function 344a further includes an analyzing function 344e and a display controlling function 344f. The analyzing function 344e is an example of the analyzing unit. The display controlling function 344f is an example of the display controlling unit.

By using the CT image data generated by the reconstruction processing function 344c, the analyzing function 344e is configured to perform the same processes as those performed by the analyzing function 125b described in the first embodiment or the modification examples. Further, the display controlling function 344f is configured to perform the same processes as those performed by the display controlling function 125c described in the first embodiment or the modification examples.

With these arrangements, for example, the display controlling function 344f is configured to display the information indicating the changes in values of the blood flow parameter along the coronary artery, by using the graph of which the vertical axis expresses the values of the blood flow parameter and of which the horizontal axis corresponds to the distance direction along the coronary artery and is configured to display the supplementary information indicating the structure of the coronary artery together with the graph.

In another example, the display controlling function 344f may be configured to display the information indicating the changes in values of the blood flow parameter along the coronary artery by using the graph of which the vertical axis expresses the values of the blood flow parameter and of which the horizontal axis corresponds to the distance direction along the coronary artery and may be configured to further display the information indicating the segments of the coronary artery on the horizontal axis of the graph.

In these situations, for example, the processing circuitry 344 is realized by using a processor. In that situation, each of the processing functions of the processing circuitry 344 is stored in the memory 341 in the form of a computer-executable program. Further, the processing circuitry 344 is configured to realize the functions corresponding to the programs by reading and executing the programs from the memory 341. In other words, when having read the programs, the processing circuitry 344 has the processing functions illustrated in FIG. 22.

With the configurations described above, in the third embodiment also, it is possible to easily understand, similarly to the first embodiment, the correspondence relationship between the positions from which the values of the blood flow parameter were derived and the positions in the coronary artery, by referring to the supplementary information together with the graph.

Other Embodiments

In the embodiments and the modification examples described above, the examples were explained in which the CT image data generated by the X-ray CT apparatus is used as the medical image data; however, possible embodiments are not limited to these examples. For instance, as long as it is possible to obtain the shape of a blood vessel from the medical image data, it is possible to use medical image data generated by other types of medical image diagnosis apparatuses such as a Magnetic Resonance Imaging (MRI) apparatus, an ultrasound diagnosis apparatus, or an X-ray diagnosis apparatus.

The medical image data used for deriving the blood flow parameter and the medical image data used for deriving the morphological parameter may be mutually-different types of medical image data. For example, the blood flow parameter may be derived on the basis of CT image data, whereas the morphological parameter may be derived on the basis of an ultrasound image generated by an ultrasound diagnosis apparatus implementing Intravascular Ultrasound (IVUS) or the like.

In the embodiments described above, the processing functions are realized by the single piece of processing circuitry in each of the apparatuses; however, possible embodiments are not limited to this example. For instance, it is also acceptable to structure processing circuitry by combining together a plurality of independent processors, so that the processing function are realized as a result of the processors executing the programs. Further, the processing functions of the processing circuitry may be realized as being distributed among, or integrated together in, one or more pieces of processing circuitry, as appropriate. Further, in the above embodiments, the example was explained in which the single piece of storage stores therein the programs corresponding to the processing functions; however, another arrangement is also acceptable in which, for example, a plurality of pieces of storage are provided in a distributed manner, so that the processing circuitry reads a corresponding program from each of the individual pieces of storage.

Further, in the embodiments described above, the example was explained in which the obtaining unit, the analyzing unit, and the display controlling unit of the present disclosure are realized by the obtaining function, the analyzing function, and the display controlling function of the processing circuitry, respectively; however, possible embodiments are not limited to this example. For instance, instead of realizing the obtaining unit, the analyzing unit, and the display controlling unit of the present disclosure by using the obtaining function, the analyzing function, and the display controlling function described in the embodiments, it is also acceptable to realize the functions by using only hardware, only software, or a combination of hardware and software.

The term "processor" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). When the processor is a CPU, for example, the processor realizes the functions by reading and executing the programs saved in the storage. In contrast, when the processor is an ASIC, for example, the functions are directly incorporated as a logic circuit in the circuit of the processor, instead of the programs being saved in the storage. Further, the processors of the present embodiments do not each necessarily have to be configured as a single piece of circuitry. It is also acceptable to structure one processor by combining together a plurality of independent circuits, so as to realize the functions thereof. Further, it is also acceptable to integrate two or more of the constituent elements illustrated in FIG. 1 into one processor so as to realize the functions thereof.

In this situation, the programs executed by the one or more processors are provided as being incorporated, in advance, in a Read Only Memory (ROM), storage, or the like.

The programs may be provided as being recorded in a computer-readable storage medium such as a Compact Disk Read-Only Memory (CD-ROM), a Flexible Disk (FD), a Compact Disk Recordable (CD-R), Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the functional units described above. In the actual hardware, as a result of a CPU reading and executing the programs from a storage medium such as a ROM, the modules are loaded into a main storage device and generated in the main storage device.

Further, the constituent elements of the apparatuses and devices in the drawings of the above embodiments and modification examples are based on functional concepts. Thus, it is not necessary to physically configure the constituent elements as indicated in the drawings. In other words, specific modes of distribution and integration of the apparatuses and devices are not limited to those illustrated in the drawings. It is acceptable to functionally or physically distribute or integrate all or a part of the apparatuses and devices in any arbitrary units, depending on various loads and the status of use. Further, all or an arbitrary part of the processing functions performed by the apparatuses and devices may be realized by a CPU and a program analyzed and executed by the CPU or may be realized as hardware using wired logic.

With regard to the processes explained in the above embodiments and modification examples, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to easily understand the correspondence relationship between the positions from which the values of the blood flow parameter were derived and the positions in the coronary artery.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A medical image processing apparatus, comprising:
processing circuitry configured to obtain medical image data related to a coronary artery of a subject;

derive a value of a blood flow parameter indicating hemodynamics of the coronary artery based on the medical image data;

display information indicating a change in the value of the blood flow parameter along the coronary artery, by using a graph of which a horizontal axis corresponds to a distance direction along the coronary artery and which represents values of the blood flow parameter;

display supplementary information indicating a structure of the coronary artery together with the graph;

display, in the graph, a first marker, a second marker, and a third marker, wherein the first marker is displayed in a position having a largest stenosis ratio of the coronary artery, the second marker is displayed in a position away from the position of the first marker toward an upstream side of the coronary artery, and the third marker is displayed in a position away from the position of the first marker toward a downstream side of the coronary artery; and display a value of a cross-sectional area of the coronary artery in the position in which the first marker is displayed, a value of a cross-sectional area of the coronary artery in the position in which the second marker is displayed, a value of a cross-sectional area of the coronary artery in the position in which the third marker is displayed, and a delta value of the blood flow parameter at a position between the position of the second marker and the position of the third marker, so that the values of the cross-sectional areas and the delta value are displayed side by side in the distance direction.

2. The medical image processing apparatus according to claim 1, wherein the processing circuitry is further configured to display information indicating a segment of the coronary artery on the horizontal axis of the graph.

3. The medical image processing apparatus according to claim 1, wherein the processing circuitry is further configured to:

derive a value of a morphological parameter indicating a morphology of the coronary artery based on the medical image data, and display, as the supplementary information, in the graph, information indicating a change in the value of the morphological parameter along the coronary artery.

4. The medical image processing apparatus according to claim 1, wherein the processing circuitry is further configured to display a tomographic image of the coronary artery along the distance direction, and display a fourth marker in a position in the tomographic image corresponding to the position in which the first marker is displayed.

5. The medical image processing apparatus according to claim 1, wherein the processing circuitry is further configured to display a tomographic image of the coronary artery along the distance direction, and display a fourth marker, a fifth marker, and a sixth marker in positions in the tomographic image respectively corresponding to the positions in which the first marker, the second marker, and the third marker are displayed.

6. The medical image processing apparatus according to claim 1, wherein the processing circuitry is further configured to (a) set a range in the distance direction along the coronary artery based on anatomical information and (b) display a value of the blood flow parameter obtained from a statistic value in the range, together with the graph.

7. The medical image processing apparatus according to claim 6, wherein the processing circuitry is further configured to display a marker indicating the range in a corresponding position in the graph.

8. The medical image processing apparatus according to claim 6, wherein the processing circuitry is further configured to set the range in units of segments of the coronary artery.

9. The medical image processing apparatus according to claim 1, wherein the processing circuitry is further configured to obtain volume data indicating functional information about a myocardium of the subject, and display the functional information about the myocardium together with the graph, based on the volume data.

10. The medical image processing apparatus according to claim 9, wherein the processing circuitry is further configured to (a) specify a dominant region of the coronary artery in the myocardium and (b) display a myocardial index value in the dominant region as the functional information about the myocardium.

11. The medical image processing apparatus according to claim 1, wherein the processing circuitry is further configured to:

derive a value of the blood flow parameter after a treatment of the coronary artery by performing a treatment simulation of the coronary artery while using the medical image data, and display, by performing a simulation using the blood flow parameter after the treatment, information indicating a change in functional information about the myocardium when the coronary artery is deformed by the treatment simulation, together with the graph.

12. The medical image processing apparatus according to claim 11, wherein the processing circuitry is further configured to:

derive functional information about the myocardium before the treatment by performing a simulation using the blood flow parameter before the treatment which is derived before the treatment simulation is performed;

derive functional information about the myocardium after the treatment by performing a simulation using the blood flow parameter after the treatment; and display the functional information about the myocardium before the treatment and the information about the myocardium after the treatment as the information indicating the change in functional information about the myocardium.

13. The medical image processing apparatus according to claim 12, wherein the processing circuitry is further configured to:

specify a dominant region of the coronary artery in the myocardium;

derive a myocardial index value before the treatment in the dominant region as the functional information about the myocardium before the treatment; and derive a myocardial index value after the treatment in the dominant region as the functional information about the myocardium after the treatment.

14. The medical image processing apparatus according to claim 1, wherein the processing circuitry is further configured to:

derive a value of the blood flow parameter after a treatment of the coronary artery by performing a treatment simulation of the coronary artery while using the medical image data, and display, in the graph, information indicating a change in the value of the blood flow parameter after the treatment.

15. The medical image processing apparatus according to claim 14, wherein the processing circuitry is further configured to:
derive a value of a morphological parameter after a treatment of the coronary artery by performing the treatment simulation, and
display, in the graph, information indicating a change in the value of the morphological parameter after the treatment.

16. A medical image processing apparatus, comprising:
processing circuitry configured to
obtain medical image data related to a coronary artery of a subject;
derive a value of a blood flow parameter indicating hemodynamics of the coronary artery based on the medical image data;
display information indicating a change in the value of the blood flow parameter along the coronary artery, by using a graph of which a horizontal axis corresponds to a distance direction along the coronary artery and which represents values of the blood flow parameter;
display information indicating a segment of the coronary artery on the horizontal axis of the graph;
display, in the graph, a first marker, a second marker, and a third marker, wherein the first marker is displayed in a position having a largest stenosis ratio of the coronary artery, the second marker is displayed in a position away from the position of the first marker toward an upstream side of the coronary artery, and the third marker is displayed in a position away from the position of the first marker toward a downstream side of the coronary artery; and
display a value of a cross-sectional area of the coronary artery in the position in which the first marker is displayed, a value of a cross-sectional area of the coronary artery in the position in which the second marker is displayed, a value of a cross-sectional area of the coronary artery in the position in which the third marker is displayed, and a delta value of the blood flow parameter at a position between the position of the second marker and the position of the third marker, so that the values of the cross-sectional areas and the delta value are displayed side by side in the distance direction.

17. A non-transitory computer-readable recording medium comprising a plurality of computer-executable instructions that cause a computer to execute a method comprising:
obtaining medical image data related to a coronary artery of a subject;
deriving a value of a blood flow parameter indicating hemodynamics of the coronary artery based on the medical image data;
displaying information indicating a change in the value of the blood flow parameter along the coronary artery, by using a graph of which a horizontal axis corresponds to a distance direction along the coronary artery and which represents values of the blood flow parameter;
displaying supplementary information indicating a structure of the coronary artery together with the graph;
displaying, in the graph, a first marker, a second marker, and a third marker, wherein the first marker is displayed in a position having a largest stenosis ratio of the coronary artery, the second marker is displayed in a position away from the position of the first marker toward an upstream side of the coronary artery, and the third marker is displayed in a position away from the position of the first marker toward a downstream side of the coronary artery; and
displaying a value of a cross-sectional area of the coronary artery in the position in which the first marker is displayed, a value of a cross-sectional area of the coronary artery in the position in which the second marker is displayed, a value of a cross-sectional area of the coronary artery in the position in which the third marker is displayed, and a delta value of the blood flow parameter at a position between the position of the second marker and the position of the third marker, so that the values of the cross-sectional areas and the delta value are displayed side by side in the distance direction.

18. A non-transitory computer-readable recording medium comprising a plurality of computer-executable instructions that cause a computer to execute a method comprising:
obtaining medical image data related to a coronary artery of a subject;
deriving a value of a blood flow parameter indicating hemodynamics of the coronary artery based on the medical image data;
displaying information indicating a change in the value of the blood flow parameter along the coronary artery, by using a graph of which a horizontal axis corresponds to a distance direction along the coronary artery and which represents values of he blood flow parameter;
displaying information indicating a segment of the coronary artery on the horizontal axis of the graph;
displaying, in the graph, a first marker, a second marker, and a third marker, wherein the first marker is displayed in a position having a largest stenosis ratio of the coronary artery, the second marker is displayed in a position away from the position of the first marker toward an upstream side of the coronary artery, and the third marker is displayed in a position away from the position of the first marker toward a downstream side of the coronary artery; and
displaying a value of a cross-sectional area of the coronary artery in the position in which the first marker is displayed, a value of a cross-sectional area of the coronary artery in the position in which the second marker is displayed, a value of a cross-sectional area of the coronary artery in the position in which the third marker is displayed, and a delta value of the blood flow parameter at a position between the position of the second marker and the position of the third marker, so that the values of the cross-sectional areas and the delta value are displayed side by side in the distance direction.

19. A medical image processing system comprising a medical image analyzing apparatus and a medical image display apparatus, wherein
the medical image analyzing apparatus includes first processing circuitry configured to obtain medical image data related to a coronary artery of a subject and to derive a value of a blood flow parameter indicating hemodynamics of the coronary artery based on the medical image data, and
the medical image display apparatus includes second processing circuitry configured to display information indicating a change in the value of the blood flow parameter along the coronary artery, by using a graph of which a horizontal axis corresponds to a distance direction along the coronary artery and which represents values of the blood flow parameter;

display supplementary information indicating a structure of the coronary artery together with the graph;

display, in the graph, a first marker, a second marker, and a third marker, wherein the first marker is displayed in a position having a largest stenosis ratio of the coronary artery, the second marker is displayed in a position away from the position of the first marker toward an upstream side of the coronary artery, and the third marker is displayed in a position away from the position of the first marker toward a downstream side of the coronary artery; and display a value of a cross-sectional area of the coronary artery in the position in which the first marker is displayed, a value of a cross-sectional area of the coronary artery in the position in which the second marker is displayed, a value of a cross-sectional area of the coronary artery in the position in which the third marker is displayed, and a delta value of the blood flow parameter at a position between the position of the second marker and the position of the third marker, so that the values of the cross-sectional areas and the delta value are displayed side by side in the distance direction.

20. A medical image processing system comprising a medical image analyzing apparatus and a medical image display apparatus, wherein the medical image analyzing apparatus includes first processing circuitry configured to obtain medical image data related to a coronary artery of a subject and to derive a value of a blood flow parameter indicating hemodynamics of the coronary artery based on the medical image data, and the medical image display apparatus includes second processing circuitry configured to display information indicating a change in the value of the blood flow parameter along the coronary artery, by using a graph of which a horizontal axis corresponds to a distance direction along the coronary artery and which represents values of the blood flow parameter;

display information indicating a segment of the coronary artery on the horizontal axis of the graph;

display, in the graph, a first marker, a second marker, and a third marker, wherein the first marker is displayed in a position having a largest stenosis ratio of the coronary artery, the second marker is displayed in a position away from the position of the first marker toward an upstream side of the coronary artery, and the third marker is displayed in a position away from the position of the first marker toward a downstream side of the coronary artery; and display a value of a cross-sectional area of the coronary artery in the position in which the first marker is displayed, a value of a cross-sectional area of the coronary artery in the position in which the second marker is displayed, a value of a cross-sectional area of the coronary artery in the position in which the third marker is displayed, and a delta value of the blood flow parameter at a position between the position of the second marker and the position of the third marker, so that the values of the cross-sectional areas and the delta value are displayed side by side in the distance direction.

* * * * *